United States Patent [19]
First et al.

[11] Patent Number: 5,776,682
[45] Date of Patent: Jul. 7, 1998

[54] MALE INFERTILITY Y-DELETION DETECTION BATTERY

[75] Inventors: Marijo Kent First, Madison, Wis.; Alexander I. Agoulnik, Houston, Tex.; Ariege Muallem, Madison, Wis.

[73] Assignee: Promega Corporation, Madison, Wis.

[21] Appl. No.: 531,556

[22] Filed: Sep. 18, 1995

Related U.S. Application Data

[63] Continuation-in-part of Ser. No. 472,416, Jun. 7, 1995.

[51] Int. Cl.$^6$ .............................. C12Q 1/68; C12P 19/34; C07H 21/04; C12N 15/00
[52] U.S. Cl. ........................ 435/6; 435/91.1; 435/91.2; 435/183; 435/270; 435/810; 536/23.1; 536/24.31; 536/24.33; 935/1; 935/8; 935/19; 935/77; 935/78
[58] Field of Search ...................... 435/6, 91.1, 91.2, 435/183, 270, 810; 536/23.1, 24.31, 24.33; 935/1, 77, 78, 8, 19

[56] References Cited

FOREIGN PATENT DOCUMENTS

| | | |
|---|---|---|
| WO87/05027 | 8/1987 | WIPO . |
| WO89/02440 | 3/1989 | WIPO . |

OTHER PUBLICATIONS

Affara, N.A., Lau, Y.-F.C., Briggs, H., Davey, P., Jones, M.H., Khwaja, O., Mithcell, M., and Sargent, C. (1994) Report of the First International Workshop on Human Y Chromosome Mapping 1994. Cytogenet Cell Genet 67, 359–402.

Agulnik, A.I., Mitchell, M.J., Lerner, J.L., Woods, D.R., and Bishop, C.E. (1994) A mouse y chromosome gene encoded by a region essential for spermatogenesis and expression of male–specific minor histocompatibility antigens. H. Mol. Gen. 3, 873, 878.

Chandley, A.C. and Cooke, H.J. (1994) Human male fertility–Y–linked genes and spermatogenesis. H. Mol. Gen. 3, 1449–1452.

Henegariu, O., Hirschmann, P., Kilian, K., Kirsch, S., Lengauet, C., Maiwald, R., Mielke, K., and Vogt, P. (1994) Rapid screening of the Y chromosome in idiopathic sterile men, diagnostic for deletions in AZF, a genetic Y factor expressed during spermatogenesis. Andrologia 26, 97–106.

Kobayashi, K., Mizuno, K., Hida, A., Komaki, R., Tomita, K., Matsishita, I., Namiki, M., Iwamoto, T., Tamura, S., Minowada, S., Nakahori, Y., and Nakagome, Y. (1994) PCR analysis of the Y chromosome long arm in azoospermic patients: evidence for a second locus required for spermatogenesis. H. Mol. Gen. 3, 1965–1967.

Ma, K., Sharkey, A., Kirsch, S., Vogt, P., Keil, R., Hargreave, T.B., McBeath, S., and Chandley, A.C. (1992) Towards the molecular localisation of the AZF locus: mapping of microdeletions in azoospermic men within 14 subintervals of interval 6 of the human Y chromosome. H. Mol. Gen. 1, 29–33.

Ma, K., Inglis, J.D., Sharley, A., Bickmore, W.A., Hill, R.E., Prosser, E.J., Speed, R.M., Thomson, E.J., Jobling, M., Taylor, K., Wolfe, J., Cooke, H.J., Hargreave, T.B., and Chandley, A.C., (1993) A Y Chromosome Gene Family with RNA–Binding Protein Homology: Candidates for the Azoospermia Factor AZF Controlling Human Spermatogenesis. Cell 75, 1287–1295.

Nagafuchi, S., Namiki, M., Nakahori, Y., Kondoh, N., Okuyama, A., and Nakagome, Y. (1993) A Minute Deletion Of The Y Chromosome In Men With Azoospermia. The J. of Urol. 150, 1155–1157.

*Primary Examiner*—Bradley L. Sisson
*Attorney, Agent, or Firm*—DeWitt Ross & Stevens S.C.

[57] ABSTRACT

The present disclosure describes a method for probing the integrity of a Y chromosome utilizing multiplex PCR reactions which amplify specific regions of the human Y chromosome which have been linked to normal fertility in human males. The method is capable of detecting deletion mutations within the Y chromosome which are predictive of human male infertility. A kit containing reagents needed to practice the method is also disclosed.

40 Claims, 14 Drawing Sheets

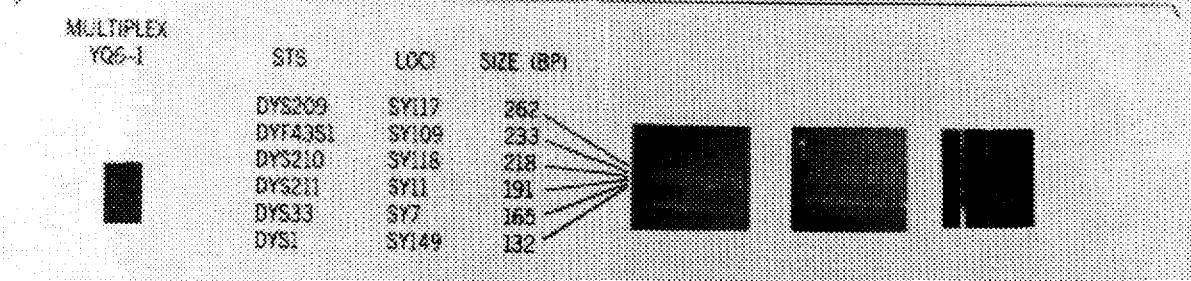
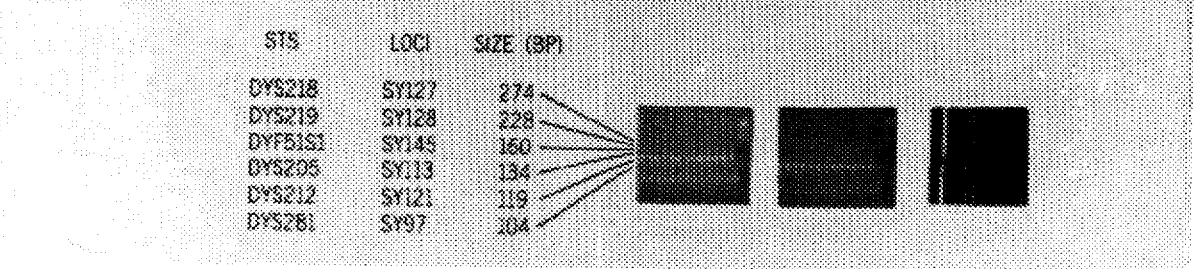

| MULTIPLEX YQ6-3 | STS | LOCI | SIZE (BP) |
|---|---|---|---|
| | DYS231 | SY105 | 301 |
| | DYS241 | SY158 | 231 |
| | DYS196 | SY102 | 216 |
| | SRY | SY14 | 190 |
| | DYS197 | SY101 | 131 |
| | DYS196 | SY100 | 111 |

| MULTIPLEX YQ5-1 | STS | LOCI | SIZE (BP) |
|---|---|---|---|
| | DYS240 | SY157 | 285 |
| | DYS238 | SY154 | 245 |
| | DYS271 | SY81 | 209 |
| | DYS230 | SY120 | 194 |
| | KAL182 | SY182 | 125 |

| STS | LOCI | SIZE (BP) |
|---|---|---|
| DYS224 | SY134 | 301 |
| DYS226 | SY136 | 235 |
| DYS222 | SY131 | 143 |
| DYS227 | SY139 | 120 |

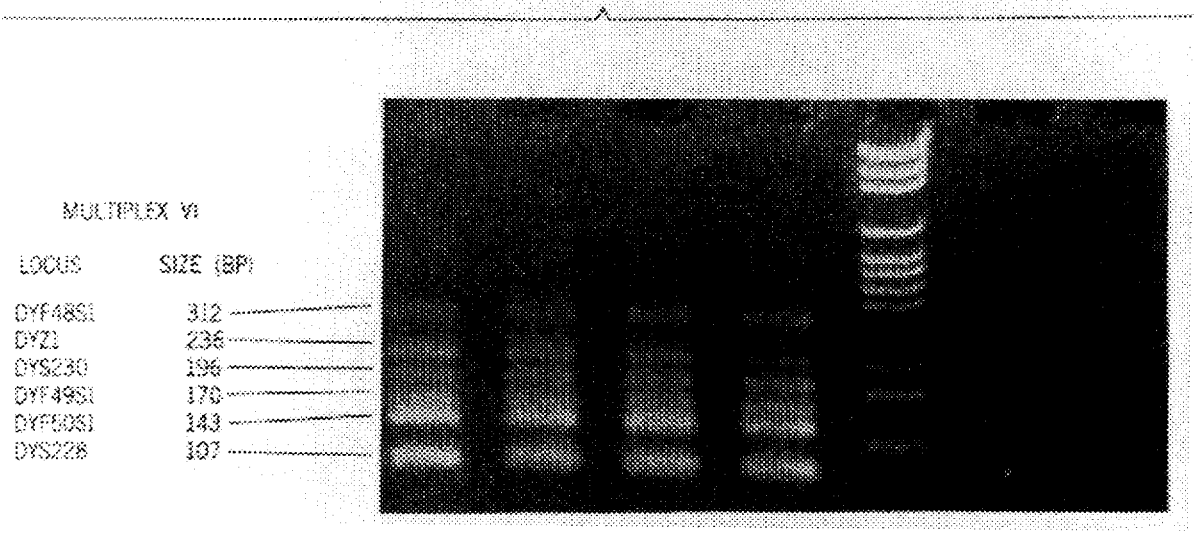

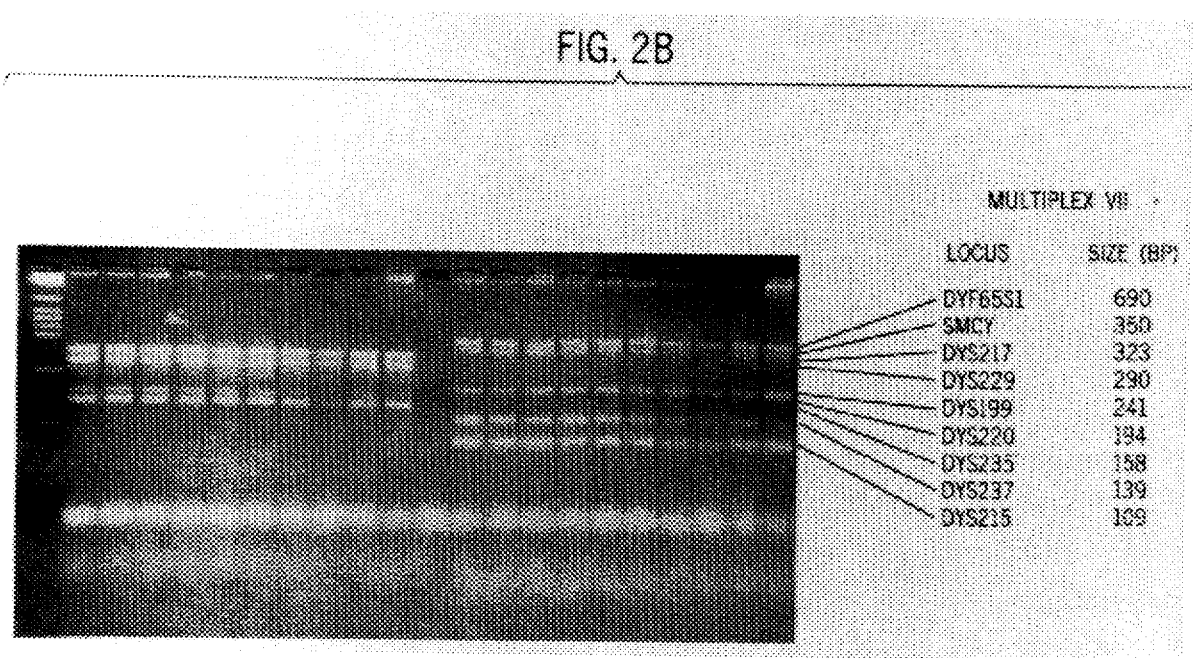

| | 3 | 5A | E | I | I | I | J | J | K | L | M | M | M | N | O | P | Q | Q | Q | 6A | A | A | A | A | B | B | C | C | D | D | E | F | F | G | 7A |
|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 |
| M | + | + | + | + | + | + | + | + | + | + | + | + | + | + | + | + | + | + | + | + | + | + | + | + | + | + | + | + | + | + | + | + | + | + |
| F | - | - | - | - | - | - | - | - | - | - | - | - | - | - | - | - | - | - | - | - | - | - | - | - | - | - | - | - | - | - | - | - | - | - |
| 1 | + | - | - | - | - | - | - | - | - | - | - | - | - | - | - | - | - | - | - | - | - | - | - | - | - | - | - | - | - | - | - | - | - | - |
| 2 | + | - | - | - | - | - | - | - | - | - | - | - | - | - | - | - | - | - | - | - | - | - | - | - | - | - | - | - | - | - | - | - | - | - |
| 3 | + | - | - | - | - | - | - | - | - | - | - | - | - | - | - | - | - | - | - | - | - | - | - | - | - | - | - | - | - | - | - | - | - | - |
| 4 | + | - | - | - | - | - | - | - | - | - | - | - | - | - | - | - | - | - | - | - | - | - | - | - | - | - | - | - | - | - | - | - | - | - |
| 5 | + | + | + | + | + | + | + | + | + | + | + | + | + | + | + | + | + | + | + | + | + | + | + | + | + | + | + | + | + | + | + | + | + | + |
| 6 | + | + | + | + | + | + | + | + | + | - | - | - | - | - | - | - | - | - | - | - | - | - | - | - | - | - | - | - | - | - | - | - | - | - |
| 7 | + | + | + | + | + | + | + | + | + | - | - | - | - | - | - | - | - | - | - | - | - | - | - | - | - | - | - | - | - | - | - | - | - | - |
| 8 | + | - | - | - | - | - | - | - | - | - | - | - | - | - | - | - | - | - | - | - | - | - | - | - | - | + | + | + | + | + | + | + | + | + |

M = Male
F = Female
1, 2, 3, 4 = XX males
5, 6, 7, 8 = patients

FIG. 3

| 3 | 5A | E | I | I | J | J | K | L | M | M | M | N | O | P | Q | Q | Q | Q | 6AA | A | A | B | C | D | D | E | F | F | F | G | 7A |
|---|----|---|---|---|---|---|---|---|---|---|---|---|---|---|---|---|---|---|-----|---|---|---|---|---|---|---|---|---|---|---|----|
| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 |
| + | + | + | + | + | + | + | + | + | + | + | + | + | + | + | + | + | + | + | + | + | + | + | + | + | + | + | + | + | + | + | + | + | + |
| + | + | + | + | + | + | + | + | + | + | + | − | − | − | − | − | − | − | − | − | − | − | − | − | − | − | − | − | − | − | − | − | − | − |

Top Line = Y Chromosomal location defined by primer pair

Boxed Numbers = Primer pair which amplifies defined segment

All Plus Row = Regions present in the Y chromosome

Plus and Minus Combination Row = Regions deleted in the aberrant Y chromosome

FIG. 10

MALE INFERTILITY Y-DELETION DETECTION BATTERY

This is a Continuation-In-Part of application Ser. No. 08/472,416, filed Jun. 7, 1995.

FIELD OF THE INVENTION

The present invention relates to detection of deletion mutations in the Y chromosome of human males. More specifically, the present invention relates to a multiplex polymerase chain reaction (PCR) assay for the detection of Y chromosome deletion mutations which are indicative of male infertility.

BIBLIOGRAPHIC CITATIONS

Complete bibliographic citations to the references discussed herein are contained in the Bibliography section, directly preceding the Sequence Listing.

DESCRIPTION OF THE PRIOR ART

Starting in 1905, when Netti Stevens and Edmund Wilson independently described the first direct evidence to support the chromosomal theory of sex determination, researchers have been studying the sex chromosomes to determine the other traits which are controlled by the expression of products encoded on the X and Y chromosomes. For instance, shortly after Stevens' and Wilson's experiments, Thomas Hunt Morgan showed that the white-eyed mutation in Drosophila is a sex-linked recessive trait localized to the X chromosome. More recently, with the advent of far more powerful gene mapping tools, many researchers have investigated the Y chromosome to determine those loci responsible for male gonadal development in newborns, and fertility in adult human males.

Of particular interest is the determination of a cause for infertility in those couples where no apparent etiology can be ascribed. It is generally believed that world wide between 2 and 8 percent of all couples are infertile. Not unexpectedly, the apparent cause of 50% of the couples experiencing difficulty having children can be traced to infertility in the male. Etiology of some of these cases of infertility can be identified by microscopic examination of the ejaculate from the male. In this manner, obvious causes of male infertility, such as no sperm in the ejaculate (azoospermia), reduced number of sperm (oligospermia), or sperm having abnormal morphology (e.g. asthenozoospermia and teratospermia) are identified. However, between 30 to 50 percent of the cases of male infertility are categorized as being idiopathic, that is, of unknown origin and having no microscopically obvious cause. This large number of infertility cases of unknown origin, and the devastating effect these have on the infertile couples has created a strong desire on the part of various researchers to obtain a better understanding of the causes of infertility in general, and on the identification of genetic factors which are associated with male infertility in particular.

To that end, many researchers are presently studying deletion mutations on the Y chromosome in azoospermic and oligospermic men. It is hoped that such studies will reveal the genetic basis for many cases of infertility now designated idiopathic. The following references all describe genetic studies of the Y chromosome in an effort to delineate those gene loci required for spermatogenesis and normal male fertility.

Two Patent Cooperation Treaty applications filed by David C. Page of the Whitehead Institute for Biomedical Research describe Y-specific DNA which can be used as probes to establish unambiguously the presence or absence of regions of the normal Y chromosome. (PCT Ser. No. WO 87/05027, published 27 Aug. 1987; and PCT Serial Number WO 89/02440, published 23 Mar. 1989.) Both of these references note a prevailing problem in analyzing the Y chromosome: Because the Y chromosome normally appears only in the haploid state, it has very little opportunity to recombine with a homolog. This makes genetic linkage studies of the Y chromosome extremely difficult, if not impossible, using conventional linkage techniques. Page also notes that attempts to establish the Y-linkage of certain traits have been inconclusive because of the difficulty in distinguishing true Y-linked inheritance from sex-limited expression of proteins encoded on the Y chromosome.

However, using cytogenetic techniques such as karyotyping and staining, there is evidence that a number of genes in addition to those required for sex determination lie on the Y chromosome. The Page patent applications describe a method to circumvent the difficulties of mapping genes to the Y chromosome by probing the genetic makeup of a test subject with probes consisting of restriction fragments of the Y chromosome from normal subjects. Using the Y-DNA probes, Page constructed a deletion map of the human Y chromosome which can be used for comparison with deletion maps constructed using the same probes in individuals with abnormal karyotypes, or, as judged by cytogenetics, to have a structurally abnormal Y chromosome.

In short, Page describes the use of his deletion map of the normal Y chromosome as the basis for selecting and cloning Y-specific DNA restriction fragments described in his PCT applications to probe the DNA of a test subject for Y-chromosome deletions. In the earlier of the Page applications, the DNA fragments are described only in terms of molecular weight and presence of restriction enzyme cleavage sites. No base pair sequences are described. The later Page application includes a single DNA nucleotide sequence of a 1.2 kb Hind III fragment from a 135 kb region of the Y chromosome. The Page references describe using the probes to map the testis determining factor (TDF) to the short arm (Yp) of the Y chromosome.

The majority of the Y-DNA sequences used as hybridization probes by Page were derived from a library made from flow-sorted Y chromosomes obtained from the National Laboratory Gene Library Project. The library consisted of a lambda phage (Charon 21A) into which fragments of Y-chromosomal DNA (obtained by complete digestion of the DNA) had been cloned. Analysis of randomly selected Y-DNA-containing clones resulted in definition of deletion intervals along the Y chromosome. DNA sequences of interest were then removed from the lambda phage and recloned into a plasmid vector (e.g., pUC8 or pUC13).

Ma et al. (1992) used a similar approach to analyze structural abnormalities in the long arm of the Y chromosome (Yq) by genomic blot hybridization. Previous cytogenetic investigations in sterile men had suggested that the location of a gene controlling spermatogenesis, called the azoospermia factor (AZF), was in band q11.23 of the Y chromosome. Furthermore, molecular mapping had localized AZF to interval 6 of the Y chromosome. Using a series of 30 DNA probes previously mapped to Yq, Ma et al. found evidence for microdeletions in interval 6 in some azoospermic men.

Using the 30 probes, Ma et al. constructed a detailed deletion map of interval 6 of the human Y chromosome. Ma et al. differentiated interval 6 into 14 sub-intervals by probing genomic blots from 21 individuals with cytogenetically-defined deletions or rearrangements on the long arm of the Y chromosome. Using the results of the 21 blots, Ma et al. were able to map the DNA probes into 14 sub-intervals of interval 6, and to order the breakpoints of the patients' altered Y chromosome unambiguously.

A further paper by Ma et al. (1993), reports the isolation and characterization of a gene family located within a Y-chromosome deletion at interval 6, sub-interval XII–XIV. Using cosmid clones isolated from Y-specific probes which map to a distal interval deletion, Ma et al. identified a potential CpG island, an indication of the presence of a gene. Using DNA sequences from a testis cDNA library isolated using the cosmid, Ma et al. found that the sequences map only to the long-arm distal euchromatin.

Ma et al. (1993) conclude that the interval 6, sub-interval XII–XIV constitutes an excellent candidate for the AZF locus. In support of this conclusion, the reference notes that partial cDNA clones map to the distal deletion interval of Yq interval 6, a region associated with azoospermia. Additionally, the expression of the genes appears to be testis specific. Ma et al. were unable to detect expression in any other tissue. Lastly, Ma et al. note that at least part of one of the genes was contained within a microdeletion of 2 oligospermic patients. The genes also show a male-specific conservation in DNA from several other mammals.

References by Nagafuchi et al. (1993), and Kobayashi et al. (1994) describe deletion analysis of the Y chromosome in men with azoospermia. In the first reference, Nagafuchi et al. analyzed the Y chromosome DNA from 50 Japanese men with idiopathic azoospermia whose Y chromosomes were cytogenetically normal. Nagafuchi et al. used 17 Y-specific DNA fragments to probe the detection of 23 loci on the Y chromosome. Additionally, they used PCR to analyze 3 additional loci, including the SRY locus. Of the 50 subjects tested, 6 had small interstitial deletions which were located within the distal portion of Yq11. Of these 6 patients, 5 lacked the same 2 loci, DYS7C and DYS1. The remaining subject displayed a larger deletion which included the DYS7C locus, but not the DYS1 locus. The authors of this reference therefore presume that the proximal part of the Yq11 interval of the Y chromosome likely encompasses the gene deletion that causes azoospermia.

A further PCR analysis of the Y chromosome by Kobayashi et al. (1994) provides evidence that a second locus is necessary for spermatogenesis. Here, 63 Japanese azoospermic or severely oligospermic men without any apparent deletion in the Y chromosome, or cell line mosaicism, were examined for the presence or absence of a total of 16 loci including 15 loci between DYS7E and DYZ1 on Yq, and the YRRM locus. With the exception of the primer sequence for YRRM1, which was modified slightly from the Ma et al. reference described immediately above, Kobayashi et al. used the same primer pairs described by Ma et al.

Chandley and Cooke (1994) describe the isolation of the Y-located RNA recognition motif genes (YRRM). This review article notes that a feature of the YRRM domain is a pair of very highly conserved motifs. This reference also notes that the YRRM gene family has at least 15 members, and that transcription of the YRRM genes has not been detected outside the testis.

Henegariu et al. (1994) describe a multiplex PCR program for detecting deletions in the long arm of the human Y chromosome in Yq11. The PCR program is designed to quickly detect small interstitial deletions in this region of the Y chromosome. Henegariu et al. begin by noting that the genetic map created by Ma et al. (above), referred to as the "Ma map," was created using two small interstitial deletions in the proximal and distal portions of Yq11. Henegariu et al. note that because these micro deletions do not overlap, a question remains as to whether the genetically-defined AZF is represented by more than one spermatogenesis gene or by a very large gene structure.

Henegariu et al. constructed five multiplex PCR experiments using 28 Yq11-specific primer pairs. The combination of primer pairs for the five multiplex PCR experiments were selected such that the difference in length between any two amplification products in a mixture should be at least 18 to 20 bp. At this length, the amplification products will separate cleanly on a normal agarose gel matrix. Additionally, in order to prevent false positives for deletions due to experimental artifacts, the primers in one mix do not recognize two juxtaposed loci on the Y chromosome. Lastly, each mixture contains primer pairs from both the proximal and distal ends of the Yq11 interval. In this manner, each multiplex mixture will have at least 1 positive internal control in the event of a larger deletion event.

The five multiplex PCR mixtures are combined in separate tubes along with the necessary reactants to form a "PCR reaction cocktail." Conventional ingredients include sterile ultrafiltered water, buffer, salt, dNTP nucleotides, and Taq DNA polymerase. The solutions are then refrigerated or frozen until use.

To run the multiplex PCR analysis, five tubes are filled with the primer mixtures I–V, respectively. An aliquot of genomic DNA from the test subject is then introduced into each of the five tubes. The tubes are then placed directly in a thermocycler preheated to 94° C. The optimal cycling conditions for 50 cycles were found to be 94° C. for 30 seconds (melting); 54° C. for 45 seconds (annealing); and 65° C. for 120 seconds (extension). The PCR reaction products are then separated on agarose gels in a known manner.

In the event of a deletion of one or more of the PCR fragments, the deletion can be confirmed by analyzing the DNA of the test subject against a single primer pair PCR experiment using the primer pair deleted from the multiplex PCR reaction. A positive PCR primer pair may be added as an internal control. If the deletion of a given PCR product is only seen in the multiplex PCR experiment, but not in the single PCR experiment, its occurrence is most likely an artifact of the PCR multiplex. Additionally, to determine if a microdeletion was caused de novo in the test subject, the same multiplex PCR reaction is performed with DNA from the test subject's father or a fertile brother. If either the father or the brother displays the same Y-chromosome deletion, the deletion is most likely due to a polymorphic event within the Y chromosome.

Henegariu et al. established the oligo primer pairs for their PCR multiplex experiment using oligo pairs from the Y-specific part of the pY6H sequence family. Additionally, oligo pairs from Y-DNA designated sY DNA loci were prepared.

The Y-DNA sequences used in the multiplex PCR experiment were selected on the basis of their location in the neighborhood of the pY6H deletion sequence. As a positive control, Henegariu et al. incorporated the sY14 DNA sequence into every experiment. Its amplification indicates the presence of the SRY gene in the distal portion of the short arm of the Y chromosome. This area is the putative sex determining locus "TDF" of the human Y chromosome. Lastly, the order and position of all Y-DNA loci used in the multiplex PCR experiments were confirmed by mapping to them to the sub-interval map of Ma et al., described above.

Henegariu et al. note that their PCR multiplex protocol does produce a number of experimental artifacts. For instance, as noted above, some Y chromosome loci are polymorphic. False deletion events are possible if the test subject has such a polymorphic point mutation in one of the PCR priming sites. Since the extension cycle of the PCR experiment will only produce amplification of DNA between correct primer sites, point mutations within a primer site will appear as a deletion event in the gel.

Another artifact will occur if there are multiple copies of a loci within the genome of the test subject. In this instance, the deletion of a repetitive DNA locus will only be detected if all sequence copies of this locus are deleted. If this is not the case, the remaining copies will be amplified. This possibility, however, can be obviated by use of an appropriate DNA blot experiment.

It is also noted that the PCR multiplex experiment may fail to detect a mutation event in the Y chromosome of sterile males. This may be due to point mutations or very small deletions within the genome which are not detected by the probes used.

It should be noted that the PCR multiplex combinations described by Henegariu et al. are wholly distinct from those described herein.

In 1994, *Cytogenetics and Cell Genetics* published a report of the First International Workshop on Human Y Chromosome Mapping 1994. This workshop was held on Apr. 2-5, 1994, in Cambridge, England. The workshop included discussions on the physical analysis of the Y chromosome, discussions dealing with genes which have been mapped to the pseudoautosomal region, genes mapped to the Y-specific regions of the Y chromosome, and comparative mapping and the evolution of the Y chromosome. The work of all of the above-noted authors was discussed during the workshop. The report notes that Ken McElreavey presented the analysis of five patients carrying a Yq deletion using Y chromosome-specific sequence-tagged sites (STS). It was noted that two of these patients exhibited Turner's Stigmata.

Agulnik et al. (1994) describe the isolation of a Y chromosome gene entitled SMCY. SMCY has a homologous gene on the X chromosome, entitled SMCX. SMCY was found to be well conserved on the Y chromosome in mouse, man, and even marsupials. Expression of the SMCY gene was studied by reverse transcriptase polymerase chain reaction (RT-PCR) using SMCY-specific PCR primer pair SH34Y/SH35Y, designed from the human Y genomic sequence. The studies indicate that the SMCY gene is a functional gene in man, and is widely expressed.

To map SMCY onto the human Y chromosome, the yeast artificial chromosome (YAC) set yOX of David Page was used. SMCY has been shown to be expressed in tissues other than the testis. Analysis of sex-reversed mice indicate that the sole mutant phenotype that can be correlated with the deletion of Smcy (the mouse homolog) is a post-natal failure of spermatogenesis. This indicates that Smcy plays some role in spermatogenesis.

As the above-references make clear, although great progress has been made in deciphering the secrets of the Y chromosome, there is a distinct need for a rapid and reproducible method to detect and quantify deletions on the Y chromosome which may be causative of male infertility, especially where no definitive etiology can be determined to account for the infertility.

As noted above, it is estimated that between two and eight percent of all couples are infertile. Of these infertile couples, approximately thirty to fifty percent of the cases of male fertility are categorized as being idiopathic. This relatively large number of cases of male infertility which cannot be ascribed a cause has created a strong desire on the part of researchers and practicing physicians to obtain a better understanding of the causes of male infertility.

At present, however, there are very few tools available beyond the microscopic examination of the ejaculate to diagnose causes of male infertility. For instance, macroscopic examination of the test subject's lifestyle and environment may reveal external causes of his infertility. Such causes may include environmental factors, substance abuse, and dietary insufficiencies.

However, as is made clear by the above references, normal development of the male gonads, and normal spermatogenesis is controlled, in large measure, by genes located on the Y chromosome. Furthermore, the above references also indicate that spermatogenesis is a very complicated process which is controlled by numerous genes located both on and off the Y chromosome. Importantly, it is known that normal spermatogenesis is impaired by certain mutations on the Y chromosome.

The structure of the Y chromosome includes the short arm (Yp), which is terminated by the pseudoautosomal region, and a long arm (Yq) terminated by the heterochromatic region. The centromere divides Yp from Yq. The euchromatic region of the Y chromosome spans from the pseudoautosomal region of Yp, across the centromere, and to the heterochromatic region of Yq. These terms shall be used herein as conventionally defined in the relevant art.

The euchromatic region of the Y chromosome has additionally been divided into intervals and sub-intervals by deletion mapping. The seven intervals and their respective sub-intervals provide reference points which aid in mapping nucleotide sequences to specific regions of the Y chromosome.

Of particular interest in the present invention are those genes which have been mapped to intervals five and six. These genes appear to play an important role in normal spermatogenesis. Lack of these genes, or mutations within these genes would appear to lead to severe oligospermia or complete azoospermia. Using the present multiplex PCR battery allows the existence and location of deletion mutations on the Y chromosome to be quickly and accurately determined. It is important to note, however, that spermatogenesis is an extremely complicated process. Analysis of azoospermic men, as in the above-discussed references, has shown that they often have deletions in both Yp, and Yq, as well as autosomal deletion mutations.

Because of the large number of deletion mutations which may give rise to male infertility, it is presently difficult, if not impossible, to ascribe a genetic etiology for many types of male infertility. However, by focusing upon those loci which have been shown to be linked to functional spermatogenesis, information can be gained as to the likelihood that a mutation at one of these loci is a factor in causing the observed infertility.

SUMMARY OF THE INVENTION

The present invention is drawn to methods and kits for the detection of microdeletions and macrodeletions which occur along the Y chromosome, and which are associated with human male infertility. The primary goal of the present invention is to provide a method and a corresponding kit which will enable a user to rapidly and reproducibly assess the integrity of specific regions on the Y chromosome which are associated with male infertility. The present invention includes a kit which is comprised of a battery of multiplexed oligonucleotides, and which may also include conventional PCR reagents, enzymes, control amplimer ladders, and control DNA.

To rapidly determine the presence of such mutations, the present invention provides a series of multiplex PCR batteries containing oligonucleotide primer pairs which are specific for chosen regions of the human Y chromosome. More specifically still, the multiplex PCR batteries may contain primer pairs which prime the amplification of loci which have been mapped to loci on the Y chromosome known or suspected to play a part in human male fertility.

The PCR primer pairs and the Y-specific loci to be amplified are chosen based upon genetic analysis using sequence-tagged sites (STS). An STS is a short stretch of DNA specifically identified by PCR. For sake of brevity, as used in herein, STS shall refer to Y chromosome-specific STS's, unless otherwise noted. Since the STS's have already been identified by PCR, it is much easier to obtain proper PCR primers for the desired loci. Moreover, the PCR multiplex protocols have been optimized to result in rapid and efficient PCR amplification.

More than 1,000 amplifications have been performed using the multiplexes disclosed herein. These amplifications reveal that the failure rate for the multiplexes is less than 2.5%.

The multiplexes have a wide number of different utilities. Primarily, the multiplexes can be used to assess the integrity of the Y chromosome in males exhibiting azoospermia or oligospermia. The multiplexes can also be used in pediatric medicine to assess the genotype of infants with ambiguous genitalia.

The multiplexes are also useful in the field of infertility, where they can be used as a diagnostic tool for couples considering in vitro fertilization (or other related fertilization treatments). Here, the couple may want to re-think their decision to proceed if the father is shown to have one or more deletions on the Y chromosome because male offspring produced by the union will also carry the deletion. Additionally, the multiplexes can be used in pre-implantation genetic diagnosis to determine if the fertilized ovum has suffered genetic alterations.

The multiplexes also have utility as diagnostic tools for researching cancer genetics and tumorigenesis. Many of the loci amplified in the disclosed multiplexes have been shown to play an as yet undetermined role in tumorigenesis. By matching their presence or absence to an abnormal phenotype of a subject, a genotype can be ascribed to the abnormal phenotype.

The multiplexes can also be used as a quality control device to test sperm being deposited at a sperm bank.

The present invention, therefore, relates to a series of multiplexed PCR batteries for determining the presence of deletion mutations on the Y chromosome.

The present invention also relates to a kit containing the above-noted PCR multiplex reaction mixtures. The kit may include all of the reagents necessary to perform the PCR multiplex analysis. In this case, the user need only provide a sample of the test subject's blood or purified DNA. The kit may include supplies of purified water, buffers, magnesium chloride, and DNA polymerase enzymes. The kit may also contain supplies of male control DNA, female control DNA, as well as molecular weight markers and amplimer control ladders which contain DNA sequences corresponding to those loci primed by the PCR primers.

In operation, DNA from the test subject is combined separately with one or more of the PCR multiplex primer pair groupings described herein which contains positive control primer pairs derived from the X chromosome. The test subject DNA is then amplified in tandem in each of the corresponding multiplex mixes with a control PCR reaction containing control normal male DNA. The test subject's amplification products are then separated, preferably on a 3% agarose gel. The amplimer control ladder(s), and optionally male control DNA and female control DNA, are then also separated on lanes adjacent to the test subject's amplification products. The presence of a deletion event in the test subject is then quickly determined by comparing the test subject's lane(s) to that of the amplimer control ladder(s). Deletion mutations within the test subject will appear as an omitted band in the test subject's gel electrophoresis lane.

The present invention provides a number of both clinical and pure research applications. In the clinical setting, the present multiplex PCR battery can be used to predict infertility in males. Additionally, by identifying the location of deletion mutations, the present invention provides the first step in the restoration of fertility by gene therapy. On the reverse of the same coin, by identifying those loci necessary for spermatogenesis, the present invention may be used to direct specific mutations designed to result in male infertility as a form of contraception.

From a research perspective, the present invention can be used to gain a better understanding of the role of the Y chromosome, and the genes thereon. Additionally, the present invention may be used to predict phenotypes resulting from a given Y chromosome deletion mutation.

In view of the above, it is a principal aim of the present invention to provide a Y-chromosome-specific multiplex PCR analysis method to determine, rapidly and reproducibly, the integrity of a Y-chromosome.

Additionally, it is an aim of the present invention to provide a kit containing reagents needed to perform the method described herein.

These and other aims and functions of the presently claimed invention will become clear upon a complete reading of the DETAILED DESCRIPTION OF THE INVENTION and attached claims.

BRIEF DESCRIPTION OF THE DRAWINGS

FIG. 1A depicts an analysis of patient DNA, normal control male DNA, and water utilizing multiplex I of the present invention. The left-hand gel depicts the analysis of an infertile male subject; this subject displays a deletion in SY11 and SY117. The two gels in the center are duplicate runs of multiplex I on a 3% Metaphor Agarose gel. In each gel, the lanes are loaded from left to right as follows: Lane 1—Molecular Weight Marker; Lane 2—Normal Male Control DNA; Lane 3—Normal Male Control DNA; Lane 4—Patient 1; Lane 5—Patient 2; Lane 6—Amplimer Ladder; Lane 7—Normal Male One; Lane 8—Normal Male Two; Lane 9—Normal Male Three; Lane 10—Patient Three; Lane 11—Patient 4; Lane 12—Patient Five; Lane 13—Amplimer Ladder; Lane 14—Nanopure Water Control. The right-hand image depicts a charge-coupled display scan from an AMBIS image analysis system which depicts the intensity of the bands depicted in the two gels described immediately above.

FIG. 1B depicts an analysis identical to that described for FIG. 1A with the exception that multiplex II of the present invention was utilized. Each gel lane is loaded from left to right as described for FIG. 1A.

FIG. 2A depicts gel electrophoresis of the amplification ladders from multiplex VI.

FIG. 2B depicts gel electrophoresis of the amplification ladders from multiplex VII.

FIG. 3 depicts deletion breakpoints from a sample of patients screened. The Y chromosome regions and intervals are shown on the horizontal axis from left to right. Normal male and female and 8 patients are depicted from top to bottom on the vertical axis.

FIG. 10 is a deletion map of the Y chromosome of twin A depicting the location of deletion events on the Y chromosome.

DEFINITIONS

Figure 1C:
FIG. 1C is an analysis identical to FIG. 1A which utilizes multiplex III of the present invention. Here, in the left-hand gel, an individual male infertile patient is depicted having deletions in intervals SY100, SY101, SY102, and SY105. The lanes of the two center gels depicted in this figure are loaded from left to right in the same manner as described above for FIG. 1A.

The following definitions are intended to assist in providing a clear and consistent understanding of the scope and detail of the terms:

Allelic ladder: a standard size marker consisting of amplified alleles from the locus.

Allele: a genetic variation associated with a segment of DNA, i.e., one of two or more alternate forms of a DNA sequence occupying the same locus.

Amplimer (control) ladder: a standard size marker consisting of amplified fragments from a plurality of different loci. Analogous to an allelic ladder, above.

Biochemical nomenclature: standard biochemical nomenclature is used herein in which the nucleotide bases are designated as adenine (A); thymine (T); guanine (G); and cytosine (C). Corresponding nucleotides are, for example, deoxyguanosine-5'-triphosphate (dGTP).

DNA polymorphism: the condition in which two or more different nucleotide sequences coexist in the same interbreeding population in a DNA sequence.

Locus (or genetic locus): a specific position on a chromosome. Alleles of a locus are located at identical sites on homologous chromosomes.

Locus-specific primer: a primer that specifically hybridizes with a portion of the stated locus or its complementary strand, at least for one allele of the locus, and does not hybridize efficiently with other DNA sequences under the conditions used in the amplification method.

Polymerase chain reaction (PCR): a technique in which cycles of denaturation, annealing with primer, and extension with DNA polymerase are used to amplify the number of copies of a target DNA sequence by $>10^6$ times. The polymerase chain reaction process for amplifying nucleic acid is covered by U.S. Pat. Nos. 4,683,195, and 4,683,202, which are incorporated herein by reference for a description of the process. A multiplex polymerase chain reaction is an analogous technique in which two or more distinct target DNA sequences are amplified simultaneously within the same sample.

Primary reaction: initial reaction using the purified human genomic DNA as template for the PCR.

Primers: two single-stranded oligonucleotides or DNA fragments which hybridize with opposing strands of a locus such that the 3' termini of the primers are in closest proximity.

Primer pair: two primers including primer 1 that hybridizes to a single strand at one end of the DNA sequence to be amplified and primer 2 that hybridizes with the other end on the complementary strand of the DNA sequence to be amplified. Also referred to as the right and left primers.

Primer site: the area of the target DNA to which a primer hybridizes.

Secondary reaction: reamplification with the same or different primer pair using a dilution of the primary reaction as template for the PCR.

DETAILED DESCRIPTION OF THE INVENTION

The present invention includes a method for assessing the integrity of a Y chromosome. The method includes the steps of first combining chromosomal DNA (either purified DNA or blood, etc.) of a test subject with at least one plurality of distinct oligonucleotide primer pairs capable of priming at least one plurality of human chromosome loci selected from the following groups of loci:

DYS209, DYF43S1, DYS210, DYS211, DYS33, DYS1, SMCX;

DYS218, DYS219, DYS51S1, DYS205, DYS212, DYS281, SMCX;

DYS201, DYS241, DYS198, SRY, DYS197, DYS196, SMCX;

DYS240, DYS238, DYS271, DYS221, KAL182, SMCX;

DYS224, DYS226, DYS222, DYS227, SMCX;

DY848S1, DYZ1, DYS230, DYF49S1, DYF50S1, DYS228, SMCX;

DYF65S1, SMCY, DYS217, DYS229, DYS199, DYS220, DYS235, DYS237, DYS215, SMCX;

YRRM1, SMCY, ZFY, BKM, SMCX;

DYS209, DYF43S1, DYS210, DYS211, DYS33, DYS1, SMCX, DAZ(1);

DYS218, DYS219, DYS212, DYS51S1, DYS205, DYS281, MIC2;

DYS201, DYS241, DYS198, SRY, DYS197, DYS196, MIC2;

DYS240, DYS271, DYS221, KAL182, DAZ(2), MIC2;

DYS224, DYS226, DYS222, DYS227, MIC2;

DYF53S1, DYS229, DYZ1, DYS230, DAZ(3), DAZ(4), DAZ(5), MIC2;

SMCY, DYS217, DYS220, DYS223, DYS7, DYS237, DYS215, MIC2;

SMCY, DYS217, DYS220, DYS7, DYS237, DYS215, DAZ(6), MIC2; and

DAZ(7), DAZ(8), DAZ(9), DAZ(10), DAZ(11), MIC2.

The at least one plurality of distinct oligonucleotide primer pairs are then amplified by at least one corresponding multiplex polymerise chain reaction to yield amplified chromosomal DNA fragments. The amplified chromosomal DNA fragments are then separated and compared to corresponding amplified chromosomal DNA fragments from normal male subjects to determine the integrity of the Y chromosome of the test subject.

More specifically, the present invention includes a method for assessing the integrity of a Y chromosome which comprises combining DNA of a test subject with ten pluralities of distinct oligonucleotide primer pairs capable of priming ten pluralities of human chromosome loci as follows:

DYS209, DYF43S1, DYS210, DYS211, DYS33, DYS1, SMCX, DAZ(1);

DYS218, DYS219, DYS212, DYF53S1, DYS205, DYS281, MIC2;

DYS201, DYS241, DYS198, SRY, DYS197, DYS196, MIC2;

DYS240, DYS271, DYS221, KAL182, DAZ(2), MIC2;

DYS224, DYS226, DYS222, DYS227, MIC2;

DYF53S1, DYS229, DYZ1, DYS230, DAZ(3), DAZ(4), DAZ(5), MIC2;

SMCY, DYS217, DYS220, DYS223, DYS7, DYS237, DYS215, MIC2;

SMCY, DYS217, DYS220, DYS7, DYS237, DYS215, DAZ(6), MIC2;

DAZ(7), DAZ(8), DAZ(9), DAZ(10), DAZ(11), MIC2; and

YRRM1, SMCY, ZFY, BKM, SMCX.

Each of the ten pluralities of distinct oligonucleotide primer pairs with its respective test subject DNA are disposed within separate receptacles. As described above, the ten pluralities of distinct oligonucleotide primer pairs are then amplified by ten corresponding multiplex polymerase chain reactions to yield amplified chromosomal DNA fragments. The amplification products are then separated, and compared to corresponding amplified chromosomal DNA fragments from normal subjects to determine the integrity of the Y chromosome of the test subject.

The present invention also includes a kit for detecting deletion mutations on a Y chromosome. The kit includes at least one first receptacle containing at least one corresponding plurality of oligonucleotide primer pairs. The kit contains at least one corresponding plurality of oligonucleotide primer pairs which is capable of priming at least one plurality of human chromosome loci selected from the following groups of loci:

DYS209, DYF43S1, DYS210, DYS211, DYS33, DYS1, SMCX, DAZ(1);

DYS218, DYS219, DYS212, DYS51S1, DYS205, DYS281, MIC2;

DYS201, DYS241, DYS198, SRY, DYS197, DYS196, MIC2;

DYS240, DYS271, DYS221, KAL182, DAZ(2), MIC2;

DYS224, DYS226, DYS222, DYS227, MIC2;

DYF53S1, DYS229, DYZ1, DYS230, DAZ(3), DAZ(4), DAZ(5), MIC2;

SMCY, DYS217, DYS220, DYS223, DYS7, DYS237, DYS215, MIC2;

SMCY, DYS217, DYS220, DYS7, DYS237, DYS215, DAZ(6), MIC2;

DAZ(7), DAZ(8), DAZ(9), DAZ(10), DAZ(11), MIC2; and

YRRM1, SMCY, ZFY, BKM, SMCX.

The kit also includes at least one second receptacle containing at least one control DNA amplimer ladder corresponding to the at least one plurality of human chromosome loci.

The kit also contains instructions for its use.

Similar to the kit described immediately above, the present invention also includes a system for assessing the integrity of specific regions on the human Y chromosome. These regions are associated with human male infertility. The system includes at least one first receptacle containing at least one corresponding plurality of oligonucleotide primer pairs. The system includes at least one corresponding plurality of oligonucleotide primer pairs which is capable of priming at least one plurality of human chromosome loci selected from the following groups of loci:

DYS209, DYF43S1, DYS210, DYS211, DYS33, DYS1, SMCX, DAZ(1);

DYS218, DYS219, DYS212, DYS51S1, DYS205, DYS281, MIC2;

DYS201, DYS241, DYS198, SRY, DYS197, DYS196, MIC2;

DYS240, DYS271, DYS221, KAL182, DAZ(2), MIC2;

DYS224, DYS226, DYS222, DYS227, MIC2;

DYF53S1, DYS229, DYZ1, DYS230, DAZ(3), DAZ(4), DAZ(5), MIC2;

SMCY, DYS217, DYS220, DYS223, DYS7, DYS237, DYS215, MIC2;

SMCY, DYS217, DYS220, DYS7, DYS237, DYS215, DAZ(6), MIC2;

DAZ(7), DAZ(8), DAZ(9), DAZ(10), DAZ(11), MIC2; and

YRRM1, SMCY, ZFY, BKM, SMCX.

The system also includes at least one second receptacle containing at least one control DNA amplimer ladder which corresponds to the at least one plurality of human chromosome loci.

A third receptacle containing normal human male DNA, and a fourth receptacle containing normal human female DNA may also be included in the system, along with instructions for its use.

Construction of the Multiplex System

Prior to constructing the multiplex system, an appropriate set of loci, primers, and amplification protocols must be selected such that amplification generates fragments of the various amplified loci which do not overlap in size or, when such overlap occurs, fragments representing different loci are detectable by separate means. In addition, the selected loci should be also compatible for use with a single amplification protocol so that specific deletion events may be corroborated. Furthermore, an internal positive control should be built into individual multiplexes to provide a positive amplification in patient, normal male and normal female samples. The specific combinations of loci described herein are unique in this application. Combinations of loci may be rejected for the above reasons, or because, in combination, one or more of the loci do not produce adequate product yield, or fragments which do not represent authentic alleles are produced in the reaction.

Successful combinations are generated by trial and error of STS combinations and by adjustment of primer concentrations to identify an equilibrium in which all included loci will be successfully amplified. In addition, unique STS primers have been generated from direct sequencing of amplimers as well as from one-direction extension in regions which flank deletion breakpoints in infertile patients. These STS's have been mapped to specific loci and incorporated into the multiplex battery.

Of particular importance in the multiplex system is the size range of amplified loci produced from the individual loci which will be analyzed together. For ease of analysis with current technologies, systems which can be detected by amplification of fragments smaller than 500 bases were preferably selected or produced from generated sequencing reactions.

Additionally, for ease of analysis, STS's were chosen which prime amplification of loci having sufficiently distinct molecular weights from each other to be cleanly and unambiguously separated by electrophoresis on agarose gels. This makes the detection of deletion events simple and apparent. Interpretation of the results of a given analysis therefore inspire confidence due to the simplicity of the analysis.

The specific STS's, Y-chromosome loci, and the size of the amplified products employed in the present invention are shown in Table 1, below.

Methodology of Performing the Analysis

To perform the present method, first, blood is drawn from the individual to be tested. This is done in conventional fashion, normally in EDTA or acid citrate. The blood is then processed to isolate the DNA contained therein. This may also be done using any conventional method, such as using Promega Corporation's Wizard® (Madison, Wis.), or by extraction using standard phenol chloroform methods. A minimum amount of about 100 ng DNA is needed per test subject. It is recommended that residual blood or DNA be stored at −20° C. for future use if deletions are detected. Approximately 100 ng of test subject and control DNA is used for each reaction tube.

For each multiplex PCR amplification, the following preferred procedure should be followed:

Into an amplification container pipette 100 ng of test subject DNA into a total template volume of 10 microliter of nanopure water, followed by 40 microliters of a selected multiplex mixture (I through XVII as shown in Table 1). The tube should then be agitated, preferably using a vortex. A suitable amount of Taq DNA polymerase is then added to the tube, and the tube is vortexed and followed by pulse centrifugation.

This same procedure is then repeated in parallel fashion using separate tubes for 1) the control normal male DNA which, upon amplification, will serve as a normal standard amplification and deletion control; and 2) the control normal female DNA.

TABLE 1

MULTIPLEX BATTERIES

| MULTIPLEX NAME | LOCI | STS | SIZE (B.P.) |
| --- | --- | --- | --- |
| I | DYS209 | SY117 | 262 |
|  | DYF43S1 | SY109 | 233 |
|  | DYS210 | SY118 | 218 |
|  | DYS211 | SY119 | 191 |
|  | DYS33 | OX7 | 165 |
|  | DYS1 | SY149 | 132 |
|  | SMCX | SXPR1 | 85 |
| II | DSY218 | SY127 | 274 |
|  | DSY219 | SY128 | 228 |
|  | DYS212 | SY121 | 190 |
|  | DYS551 | SY155 | 160 |
|  | DYS205 | SY113 | 134 |
|  | DYS201 | SY97 | 104 |
|  | SMCX | SXPR1 | 85 |
| III | DYS201 | SY105 | 301 |
|  | DYS241 | SY158 | 231 |
|  | SYS198 | SY102 | 218 |
|  | SRY | SYPR2 | 190 |
|  | DYS197 | SY101 | 131 |
|  | DYS196 | SY100 | 111 |
|  | SMCX | SXPR1 | 85 |
| IV | DYS240 | SY157 | 285 |
|  | DYS238 | SY154 | 245 |
|  | DYS271 | SY81 | 209 |
|  | DYS221 | SY130 | 173 |
|  | KAL182 | SY182 | 125 |
|  | SMCX | SXPR1 | 85 |
| V | DYS224 | SY134 | 301 |
|  | DYS226 | SY136 | 235 |
|  | SYS222 | SY131 | 143 |
|  | DYS227 | SY139 | 120 |
|  | SMCX | SXPR1 | 85 |
| VI | DYF48S1 | SY137 | 312 |
|  | DYZ1 | SY160 | 236 |
|  | DYS230 | SY142 | 196 |
|  | DYF49S1 | SY138 | 170 |
|  | DYF50S1 | SY144 | 143 |
|  | DYS228 | SY140 | 107 |
|  | SMCX | SXPR1 | 85 |
| VII | DYF65S1 | SY164 | 690 |
|  | SMCY | SYPR3 | 350 |
|  | DYS217 | SY126 | 323 |
|  | DYS229 | SY141 | 290 |
|  | DYS199 | SY103 | 241 |
|  | DYS220 | SY129 | 194 |
|  | DYS235 | SY150 | 158 |
|  | DYS237 | SY153 | 139 |
|  | DYS215 | SY124 | 109 |
|  | SMCX | SXPR1 | 85 |
| VIII | YRRM1 | SYPR4 | 800 |
|  | SMCY | SYPR5 | 600 |

TABLE 1-continued

MULTIPLEX BATTERIES

| MULTIPLEX NAME | LOCI | STS | SIZE (B.P.) |
|---|---|---|---|
| | ZFY | SYPR7 | 420 |
| | BKM | SYPR6 | 230 |
| | SMCX | SXPR1 | 85 |
| IX | DYS209 | SY117 | 262 |
| | DYF43S1 | SY109 | 233 |
| | DYS210 | SY118 | 218 |
| | DYS211 | SY119 | 191 |
| | DYS33 | OX7 | 165 |
| | DYS1 | SY149 | 133 |
| | SMCX | SXPR1 | 126 |
| | DAZ(1) | SY269 | 94 |
| X | DSY218 | SY127 | 274 |
| | DSY219 | SY128 | 228 |
| | DYS212 | SY121 | 190 |
| | DYS551 | SY155 | 160 |
| | DYS205 | SY113 | 134 |
| | DYS281 | SY97 | 104 |
| | MIC2 | SY4 | 80 |
| XI | DYS201 | SY105 | 301 |
| | DYS241 | SY158 | 231 |
| | SYS198 | SY102 | 218 |
| | SRY | SYPR2 | 190 |
| | DYS197 | SY101 | 131 |
| | DYS196 | SY100 | 111 |
| | MIC2 | SY4 | 80 |
| XII | DYS240 | SY157 | 285 |
| | DYS271 | SY81 | 209 |
| | DYS221 | SY130 | 173 |
| | KAL182 | SY182 | 125 |
| | DAZ(2) | SY201 | 99 |
| | MIC2 | SY4 | 80 |
| XIII | DYS224 | SY134 | 301 |
| | DYS226 | SY136 | 235 |
| | SYS222 | SY131 | 143 |
| | DYS227 | SY139 | 120 |
| | MIC2 | SY4 | 80 |
| XIV | DYF53S1 | SY155 | 349 |
| | DYS229 | SY141 | 290 |
| | DYZ1 | SY160 | 236 |
| | DYS230 | SY142 | 196 |
| | DAZ(3) | SY231 | 149 |
| | DAZ(4) | SY202 | 121 |
| | DAZ(5) | SY262 | 100 |
| | MIC2 | SY4 | 80 |
| XV | SMCY | SYPR3 | 350 |
| | DYS217 | SY126 | 323 |
| | DYS220 | SY129 | 194 |
| | DYS223 | SY133 | 177 |
| | DYS7 | SY132 | 159 |
| | DYS237 | SY153 | 139 |
| | DYS215 | SY124 | 109 |
| | MIC2 | SY4 | 80 |
| XVI | SMCY | SYPR3 | 350 |
| | DYS217 | SY126 | 323 |
| | DYS220 | SY129 | 194 |
| | DYS7 | SY132 | 159 |
| | DYS237 | SY153 | 139 |
| | DYS215 | SY124 | 109 |
| | DAZ(6) | SY248 | 94 |
| | MIC2 | SY4 | 80 |
| XVII | DAZ(7) | SY254 | 350 |
| | DAZ(8) | SY242 | 233 |
| | DAZ(9) | SY239 | 200 |
| | DAZ(10) | SY208 | 140 |
| | DAZ(11) | SY255 | 126 |
| | MIC2 | SY4 | 80 |

The above procedure is repeated for each of the multiplexes which is performed. Thus, at a minimum, the complete battery of seventeen multiplexes as listed in Table 1 would include, for each multiplex, a single tube of the test subject's DNA, and a corresponding tube of control amplimer ladder DNA containing normal fertile male DNA, each tube containing all components needed for optimal amplification. Optionally, for each of the given multiplexes I through XVII, a negative (human male contamination) control consisting of 100 ng human female DNA plus the respective multiplex mix may also be tested. As an added precaution against extraneous contamination, 10 microliters of included nanopure water may also be used as a template control. All components should be kept on ice during preparation. Preferably, sufficient reagents for amplification of 10 patients and their controls is provided. It is recommended, however, that patients to be tested are batched in groups of 5 to 10. If this is done, a set of controls may be only necessary for the first patient in a given "batched" PCR amplification. Blood can be stored for up to four weeks at 4° C. and DNA can be stored indefinitely at −20° C.

To amplify, one drop of sterile mineral oil is added to each tube. The tubes are then closed and placed on a licensed thermocycler and amplified as follows: initial denaturation: 95° C. for 2.5 minutes; denaturation: 95° C. for one minute; annealing: 61° C. for 1 minute; extension: 72° C. for 1 minute. The amplification protocol should be repeated for thirty-five cycles.

After amplification, the samples are held at 4° C. The amplification products are separated on a standard 3% Metaphor or NuSeive agarose gel using conventional and well-known electrophoretic procedures. After electrophoresis is complete, the gel is stained with ethidium bromide according to standard protocols, visualized on a UV light box, and photographed. The photographs are then analyzed for the presence of deletion events.

TABLE 2

Preferred Oligonucleotide Primer Sequences

| MULTI-PLEX | PRIMER 1 | PRIMER 2 | PRIMER CONC'TRATION (PER PRIMER) |
|---|---|---|---|
| I | Seq. I.D. No. 1 | Seq. I.D. No. 2 | 100 pM |
| | Seq. I.D. No. 3 | Seq. I.D. No. 4 | 100 pM |
| | Seq. I.D. No. 5 | Seq. I.D. No. 6 | 100 pM |
| | Seq. I.D. No. 7 | Seq. I.D. No. 8 | 100 pM |
| | Seq. I.D. No. 9 | Seq. I.D. No. 10 | 100 pM |
| | Seq. I.D. No. 11 | Seq. I.D. No. 12 | 100 pM |
| | Seq. I.D. No. 13 | Seq. I.D. No. 14 | 80–100 pM |
| II | Seq. I.D. No. 15 | Seq. I.D. No. 16 | 100 pM |
| | Seq. I.D. No. 17 | Seq. I.D. No. 18 | 100 pM |
| | Seq. I.D. No. 19 | Seq. I.D. No. 20 | 100 pM |
| | Seq. I.D. No. 21 | Seq. I.D. No. 22 | 25 pM |
| | Seq. I.D. No. 23 | Seq. I.D. No. 24 | 50 pM |
| | Seq. I.D. No. 25 | Seq. I.D. No. 26 | 100 pM |
| | Seq. I.D. No. 13 | Seq. I.D. No. 14 | 80–100 pM |
| III | Seq. I.D. No. 27 | Seq. I.D. No. 28 | 100 pM |
| | Seq. I.D. No. 29 | Seq. I.D. No. 30 | 100 pM |
| | Seq. I.D. No. 31 | Seq. I.D. No. 32 | 100 pM |
| | Seq. I.D. No. 33 | Seq. I.D. No. 34 | 100 pM |
| | Seq. I.D. No. 35 | Seq. I.D. No. 36 | 100 pM |
| | Seq. I.D. No. 37 | Seq. I.D. No. 38 | 200 pM |
| | Seq. I.D. No. 13 | Seq. I.D. No. 14 | 80–100 pM |
| IV | Seq. I.D. No. 39 | Seq. I.D. No. 40 | 100 pM |
| | Seq. I.D. No. 41 | Seq. I.D. No. 42 | 100 pM |
| | Seq. I.D. No. 43 | Seq. I.D. No. 44 | 100 pM |
| | Seq. I.D. No. 45 | Seq. I.D. No. 46 | 100 pM |
| | Seq. I.D. No. 47 | Seq. I.D. No. 48 | 100 pM |
| | Seq. I.D. No. 13 | Seq. I.D. No. 14 | 80–100 pM |
| V | Seq. I.D. No. 49 | Seq. I.D. No. 50 | 100 pM |
| | Seq. I.D. No. 51 | Seq. I.D. No. 52 | 100 pM |
| | Seq. I.D. No. 53 | Seq. I.D. No. 54 | 100 pM |
| | Seq. I.D. No. 55 | Seq. I.D. No. 56 | 100 pM |
| | Seq. I.D. No. 13 | Seq. I.D. No. 14 | 80–100 pM |
| VI | Seq. I.D. No. 57 | Seq. I.D. No. 58 | 100 pM |
| | Seq. I.D. No. 59 | Seq. I.D. No. 60 | 100 pM |

TABLE 2-continued

Preferred Oligonucleotide Primer Sequences

| MULTI-PLEX | PRIMER 1 | PRIMER 2 | PRIMER CONC'TRATION (PER PRIMER) |
|---|---|---|---|
|  | Seq. I.D. No. 61 | Seq. I.D. No. 62 | 100 pM |
|  | Seq. I.D. No. 63 | Seq. I.D. No. 64 | 100 pM |
|  | Seq. I.D. No. 65 | Seq. I.D. No. 66 | 100 pM |
|  | Seq. I.D. No. 67 | Seq. I.D. No. 68 | 100 pM |
|  | Seq. I.D. No. 13 | Seq. I.D. No. 14 | 80–100 pM |
| VII | Seq. I.D. No. 69 | Seq. I.D. No. 70 | 100 pM |
|  | Seq. I.D. No. 71 | Seq. I.D. No. 72 | 100 pM |
|  | Seq. I.D. No. 73 | Seq. I.D. No. 74 | 100 pM |
|  | Seq. I.D. No. 75 | Seq. I.D. No. 76 | 100 pM |
|  | Seq. I.D. No. 77 | Seq. I.D. No. 78 | 100 pM |
|  | Seq. I.D. No. 79 | Seq. I.D. No. 80 | 100 pM |
|  | Seq. I.D. No. 81 | Seq. I.D. No. 82 | 100 pM |
|  | Seq. I.D. No. 83 | Seq. I.D. No. 84 | 100 pM |
|  | Seq. I.D. No. 85 | Seq. I.D. No. 86 | 100 pM |
|  | Seq. I.D. No. 13 | Seq. I.D. No. 14 | 80–100 pM |
| VIII | Seq. I.D. No. 87 | Seq. I.D. No. 88 | 100 pM |
|  | Seq. I.D. No. 89 | Seq. I.D. No. 90 | 100 pM |
|  | Seq. I.D. No. 91 | Seq. I.D. No. 92 | 100 pM |
|  | Seq. I.D. No. 93 | Seq. I.D. No. 94 | 100 pM |
|  | Seq. I.D. No. 13 | Seq. I.D. No. 14 | 80–100 pM |
| IX | Seq. I.D. No. 1 | Seq. I.D. No. 2 | 53 pM |
|  | Seq. I.D. No. 3 | Seq. I.D. No. 4 | 53 pM |
|  | Seq. I.D. No. 5 | Seq. I.D. No. 6 | 35 pM |
|  | Seq. I.D. No. 7 | Seq. I.D. No. 8 | 53 pM |
|  | Seq. I.D. No. 9 | Seq. I.D. No. 10 | 53 pM |
|  | Seq. I.D. No. 11 | Seq. I.D. No. 12 | 35 pM |
|  | Seq. I.D. No. 13 | Seq. I.D. No. 14 | 26.5 pM |
|  | Seq. I.D. No. 95 | Seq. I.D. No. 96 | 53 pm |
| X | Seq. I.D. No. 15 | Seq. I.D. No. 16 | 73 pM |
|  | Seq. I.D. No. 17 | Seq. I.D. No. 18 | 73 pM |
|  | Seq. I.D. No. 19 | Seq. I.D. No. 20 | 73 pM |
|  | Seq. I.D. No. 21 | Seq. I.D. No. 22 | 36.5 pM |
|  | Seq. I.D. No. 23 | Seq. I.D. No. 24 | 36.5 pM |
|  | Seq. I.D. No. 25 | Seq. I.D. No. 26 | 73 pM |
|  | Seq. I.D. No. 97 | Seq. I.D. No. 98 | 36.5 pM |
| XI | Seq. I.D. No. 27 | Seq. I.D. No. 28 | 53 pM |
|  | Seq. I.D. No. 29 | Seq. I.D. No. 30 | 26.5 pM |
|  | Seq. I.D. No. 31 | Seq. I.D. No. 32 | 53 pM |
|  | Seq. I.D. No. 33 | Seq. I.D. No. 34 | 26.5 pM |
|  | Seq. I.D. No. 35 | Seq. I.D. No. 36 | 159 pM |
|  | Seq. I.D. No. 37 | Seq. I.D. No. 38 | 53 pM |
|  | Seq. I.D. No. 97 | Seq. I.D. No. 98 | 26.5 pM |
| XII | Seq. I.D. No. 39 | Seq. I.D. No. 40 | 62 pM |
|  | Seq. I.D. No. 43 | Seq. I.D. No. 44 | 62 pM |
|  | Seq. I.D. No. 45 | Seq. I.D. No. 46 | 62 pM |
|  | Seq. I.D. No. 47 | Seq. I.D. No. 48 | 62 pM |
|  | Seq. I.D. No. 99 | Seq. I.D. No. 100 | 124 pM |
|  | Seq. I.D. No. 97 | Seq. I.D. No. 98 | 31 pM |
| XIII | Seq. I.D. No. 49 | Seq. I.D. No. 50 | 89 pM |
|  | Seq. I.D. No. 51 | Seq. I.D. No. 52 | 89 pM |
|  | Seq. I.D. No. 53 | Seq. I.D. No. 54 | 89 pM |
|  | Seq. I.D. No. 55 | Seq. I.D. No. 56 | 89 pM |
|  | Seq. I.D. No. 97 | Seq. I.D. No. 98 | 44.5 pM |
| XIV | Seq. I.D. No. 115 | Seq. I.D. No. 116 | 57 pM |
|  | Seq. I.D. No. 75 | Seq. I.D. No. 76 | 57 pM |
|  | Seq. I.D. No. 59 | Seq. I.D. No. 60 | 228 pM |
|  | Seq. I.D. No. 61 | Seq. I.D. No. 62 | 57 pM |
|  | Seq. I.D. No. 117 | Seq. I.D. No. 118 | 57 pM |
|  | Seq. I.D. No. 119 | Seq. I.D. No. 120 | 228 pM |
|  | Seq. I.D. No. 121 | Seq. I.D. No. 122 | 57 pM |
|  | Seq. I.D. No. 97 | Seq. I.D. No. 98 | 57 pM |
| XV | Seq. I.D. No. 71 | Seq. I.D. No. 72 | 47 pM |
|  | Seq. I.D. No. 73 | Seq. I.D. No. 74 | 94 pM |
|  | Seq. I.D. No. 79 | Seq. I.D. No. 80 | 188 pM |
|  | Seq. I.D. No. 81 | Seq. I.D. No. 82 | 188 pM |
|  | Seq. I.D. No. 101 | Seq. I.D. No. 102 | 47 pM |
|  | Seq. I.D. No. 83 | Seq. I.D. No. 84 | 47 pM |
|  | Seq. I.D. No. 85 | Seq. I.D. No. 86 | 94 pM |
|  | Seq. I.D. No. 97 | Seq. I.D. No. 98 | 47 pM |
| XVI | Seq. I.D. No. 71 | Seq. I.D. No. 72 | 53 pM |
|  | Seq. I.D. No. 73 | Seq. I.D. No. 74 | 106 pM |
|  | Seq. I.D. No. 79 | Seq. I.D. No. 80 | 212 pM |
|  | Seq. I.D. No. 101 | Seq. I.D. No. 102 | 53 pM |
|  | Seq. I.D. No. 83 | Seq. I.D. No. 84 | 106 pM |
|  | Seq. I.D. No. 85 | Seq. I.D. No. 86 | 106 pM |
|  | Seq. I.D. No. 103 | Seq. I.D. No. 104 | 106 pM |
|  | Seq. I.D. No. 97 | Seq. I.D. No. 98 | 53 pM |
| XVII | Seq. I.D. No. 105 | Seq. I.D. No. 106 | 546 pM |
|  | Seq. I.D. No. 107 | Seq. I.D. No. 108 | 136.5 pM |
|  | Seq. I.D. No. 109 | Seq. I.D. No. 110 | 546 pM |
|  | Seq. I.D. No. 111 | Seq. I.D. No. 112 | 91 pM |
|  | Seq. I.D. No. 113 | Seq. I.D. No. 114 | 91 pM |
|  | Seq. I.D. No. 97 | Seq. I.D. No. 98 | 182 pM |

The preferred oligonucleotide locus-specific primer sequences for use in the present invention, and the preferred primer concentration (concentration per primer) in the amplification reaction are listed in Table 2, above. Table 2 corresponds with Table 1. For example, Seq. I.D. Nos. 1 and 2 of Table 2 are locus-specific primer pairs for the DYS209 locus as shown in Table 1. It must be noted that these primer concentrations are the preferred concentrations. Variations may be made in the concentration of the various primer concentrations to optimize the PCR.

The Test Kit

The kit of the present invention is designed to detect small Y chromosome-linked deletions which are associated with the various types of human male infertility in a reliable and reproducible manner with built-in internal controls. In the preferred embodiment of the kit, the kit includes all of the necessary reagents and containers to successfully practice the method, while simultaneously minimizing the possibility of both human errors and experimental errors. In the most preferred embodiment, the kit includes the STS oligonucleotide primer pairs listed in Table 2 packaged together in a ready to use, user-friendly format which includes the following items:

(a) Ten multiplex mixes which contain oligonucleotide pairs capable of priming amplification of the loci detailed in Table 1, reaction buffer, magnesium, dNTP's, and sterile water combined together at pre-optimized, PCR-suitable concentrations and ratios. Preferably, sufficient multiplex mix is provided to allow the end user to assay ten patients and their corresponding controls. The ten multiplex mixes are placed in separate containers, and labeled accordingly.

(b) Ten control amplimer ladders to be used as gel electrophoresis molecular weight control markers. The ten control amplimer ladders correspond with the ten multiplex mixes described in (a) above. The ten control amplimer ladders are placed in separate containers, and labeled accordingly. In practice, each multiplex is separated and resolved on an agarose gel with its respective control male amplification and amplimer ladder being electrophoresed on a parallel lane for ease of size and quality comparison.

(c) Control normal male DNA. (Promega Part #G147, Madison, Wis.).

(d) Control normal female DNA. (Promega Part #G152, Madison, Wis.).

(e) Nanopure water.

The kit may also include a number of optional items to increase the convenience of the kit. Included among these additional optional items are Taq DNA polymerase, sterile mineral oil, a plurality of pre-sterilized 0.5 ml microfuge tubes, molecular weight control markers (for instance PGEM Promega Part #DG17A), and electrophoresis gel loading dye (for instance Promega Part #DV433A). All of the elements of the kit are then packaged within a single, user-friendly container along with instructions on how to properly use the kit.

As noted above, the preferred individual oligonucleotide locus-specific primer pairs for multiplexes I–XVII, and their preferred concentrations are listed in Table 2.

Advantages of the Kit

The kit provides an easy and simple method for determining the presence of deletion mutations on the Y chromosome in areas which have been tied to abnormal spermatogenesis. The various STS's combined in each multiplex were selected: 1) because of the absence of contaminating X-chromosome, autosome, or duplicated Y-linked sequences; 2) because of their compatibility with one another within a multiplexed reaction; 3) because the deletions associated with specific amplimers have not been shown to be associated with a statistically significant sampling of fertile males; and 4) because they amplify a DNA product which is sufficiently different in size from the other products amplified within the multiplex such that the amplified fragments separate cleanly on conventional agarose gels. This makes analyzing the gels for deletion mutations quick and simple, and minimizes the risk of false positive deletion events or experimental artifacts masking the presence of a deletion event (i.e. a false negative). A special effort has been made to provide unique STS's from selected regions in which a high frequency of deletions associated with infertility (minimally, azoospermia and oligospermia) is observed.

Of paramount importance is that the kit be "user friendly," and extremely simple in use. This minimizes the chance of human error, while simultaneously increasing the accuracy and reproducibility of the assay. This is accomplished by combining the necessary reagents and containers therefor in a single kit, along with concise instructions for its use. In this manner, the present invention allows for the assay of the Y chromosome of a male test subject for deletion mutations in a matter of hours.

Moreover, because the test kit employs the PCR methodology, a widely accepted and respected experimental technique, its reliability and acceptance by those of skill in the art is assured.

EXPERIMENTAL EXAMPLES

The following examples are provided for illustrative purposes only to aid in a complete understanding of the presently claimed invention. It is understood that the following examples do not limit the claimed invention in any manner.

Population Sampling

Table 3 shows a summary of the success rate of the respective multiplexes on a sample population of 291 individuals (multiplexes I–V), and 45 individuals (multiplexes VI–VIII). As can be seen from this table, the success rate for multiplexes I–VI are all greater than 95%, with the success rate for multiplex I being 100%. The success rate for multiplexes VII and VIII were both 91% in this study.

TABLE 3

Multiplex Data Summary

| Multiplex | # Normals | # Failures | % Success |
|---|---|---|---|
| I | 291 | 0 | 100% |
| II | 291 | 10 | 97.1% |
| III | 291 | 3 | 99.0% |
| IV | 291 | 9 | 96.9% |
| V | 291 | 12 | 95.9% |
| VI | 45 | 1 | 95.5% |
| VII | 45 | 2 | 91.0% |
| VIII | 45 | 2 | 91.0% |

Table 4, below, list population studies of 520 phenotypically normal, fertile males (blood provided by the Red Cross), and patient samplings from four physicians' practice groups dealing with infertile male patients. The Red Cross sampling of 400 fertile males showed no deletions by analysis with the present multiplex battery. The largest of the physicians' patient groups, 175 patients, displayed a 6.6% rate of Y chromosome deletion using the present multiplex analysis. For the entire study as summarized in Table 4, 11.5% of the population tested displayed Y chromosome deletion mutations.

TABLE 4

Samples Tested

| Source # | Normals | # Deletions | # Patients | Phenotype | Percent Deletions |
|---|---|---|---|---|---|
| Red Cross | 520 | 0 | | fertile/male | 0 |
| Physician #1 | | 9 | 175* | infertile/male | 5.1 |
| Physician #2 | | 7 | 16 | infertile/male | 43.8 |
| Physician #3 | | 3 | 6 | infertile/male | 50.0 |
| Physician #4 | | 5 | 42 | infertile/male | 11.9 |
| TOTALS | 520 | 24 | 239 | | 10.0% |

*This represents 175 CONSECUTIVE patients from a Urologic Surgery Practice and includes patients with structural abnormalities and infertility due to infectious disease.

Table 5, below, tabulates the success rate of multiplexes VIII–XVII when used to analyze the 520 blood samples from normal fertile males obtained from the Red Cross as described above.

TABLE 5

Multiples Data Summary

| Multiplex | Size | # Normals | Success |
|---|---|---|---|
| IX | 8-plex | 520 | 99.1% |
| X | 7-plex | 520 | 96.5% |
| XI | 7-plex | 520 | 99.2% |
| XII | 7-plex | 520 | 96.2% |
| XIII | 5-plex | 520 | 96.9% |
| XIV | 8-plex | 520 | 97.1% |
| XV | 8-plex | 520 | 95.7% |
| VIII | 5-plex | 520 | 97.0% |
| XVI | 8-plex | 520 | 97.5% |
| XVII | 6-plex | 520 | 94.2% |

The following examples illustrate how the presently claimed invention functions to detect Y chromosome deletion events. The examples are for illustrative purposes only, and do not limit the scope of the invention described and claimed herein in any fashion.

EXAMPLE 1

Analysis Utilizing Multiplexes I–V

Figure 1D:
FIG. 1D depicts an analysis identical to that described for FIG. 1A using multiplex IV of the present invention. Here, the left-hand gel depicts an individual male patient having deletions in intervals SY182, SY120, and SY81. The lanes of the right-hand gel are loaded from left to right in the same fashion as described above for FIG. 1A.
Figure 1E:
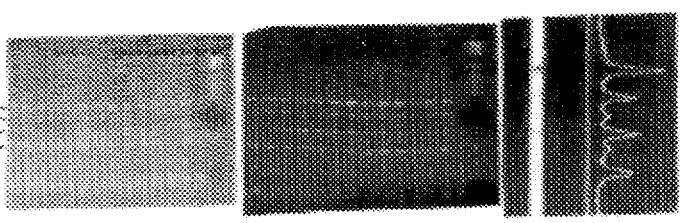
FIG. 1E depicts an analysis as described for FIG. 1A utilizing multiplex V of the present invention. The gel lanes are loaded from left to right as described above for FIG. 1A.

Here, five patients, designated patients 1 through 5, and three normal adult males were analyzed using multiplexes I–V as shown in FIG. 1. As shown in FIG. 1, the designations for the STS's, loci, and the base pair size of the amplified fragments are shown from the top of the page to the bottom, respectively. The nine gels occupying the center of FIG. 1 are the results for each analysis. Multiplexes I–V run from the top of the figure to the bottom, respectively. Multiplexes I, II, III, and V were run in duplicate. All of the DNA preparation and amplification was performed using the procedure detailed above. The gels shown in the left-most portion of FIG. 1 depict deletion events which occurred in multiplexes I, III, and IV, respectively.

The graphs at the right-most portion of FIG. 1 are AMBIS scans showing the intensity of each of the amplified bands.

EXAMPLE 2

Genetic Analysis Using Multiplexes VI and VII

Example 2 was performed in an identical fashion to Example 1, with the exception that multiplexes VI and VII were used. The results are shown in FIGS. 2A and 2B, respectively. As in Example 1, the standard protocol was used to prepare the DNA, and to electrophorese and analyze the gels.

EXAMPLE 3

Positive, X-linked Control Using SMCX

Figure 2C:
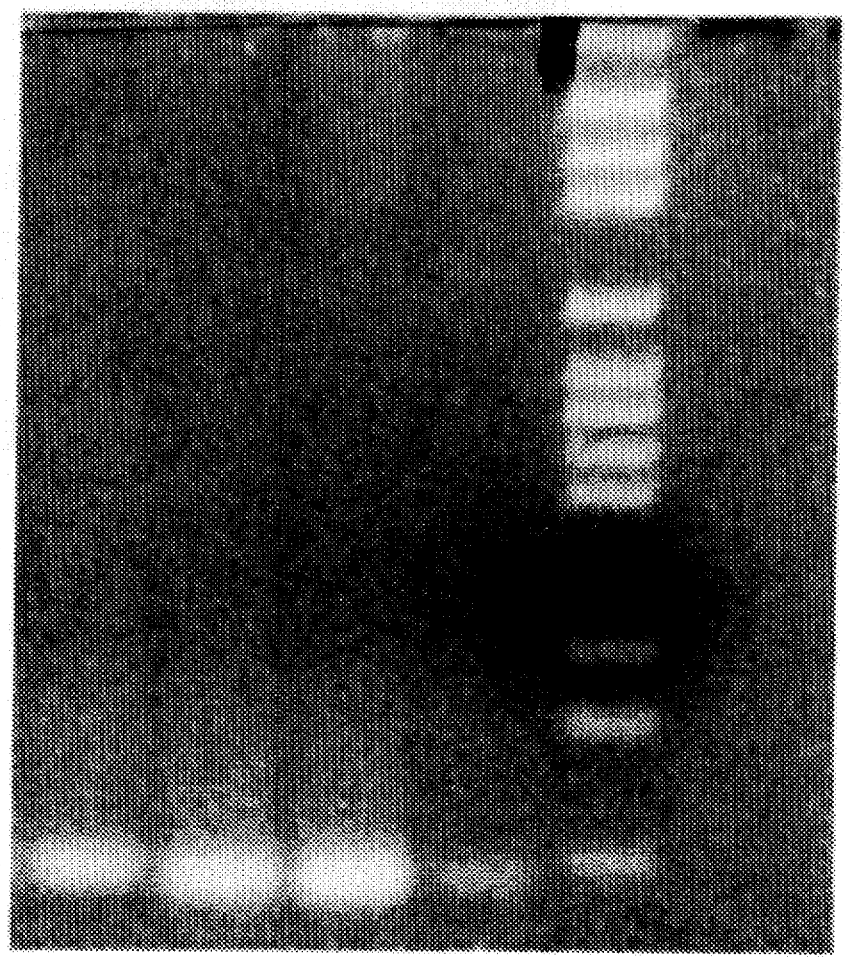
FIG. 2C depicts the positive, X-linked control, SMCX.

In this example, an X-linked locus, SMCX, is used as a positive control. Here, the SMCX primer pairs were developed alone, according to the standard protocol. The resultant gel is shown in FIG. 2C.

EXAMPLE 4

Analysis of Azoospermic XX Male Using Multiplex III

Figure 4:
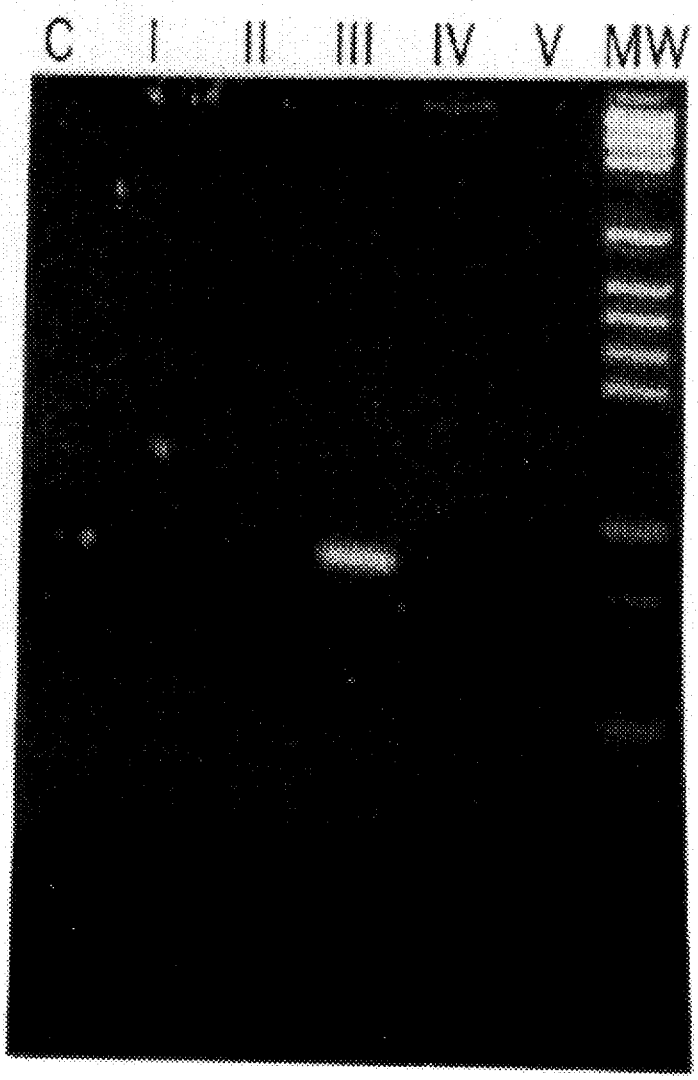
FIG. 4 depicts an azoospermic XX male who had a translocation of the distal portion of the Y chromosome onto the X chromosome and was found to be negative for all of the Y with the exception of SRY in Multiplex III.

In this example, an azoospermic XX male was analyzed using multiplex III. This patient has a translocation of the distal portion of the Y chromosome onto the X chromosome. As shown in FIG. 4, the resulting analysis with multiplex III showed this patient to be completely negative for all of the Y chromosome loci contained in multiplex III, with the exception of SRY.

EXAMPLE 5

Analysis of Prenatal Twins Utilizing Multiplexes I–V

In Example 5, DNA was extracted from amniocytes and analyzed using multiplexes I–V in using the above-described protocol. The results are shown in FIG. 5.

Figure 5:
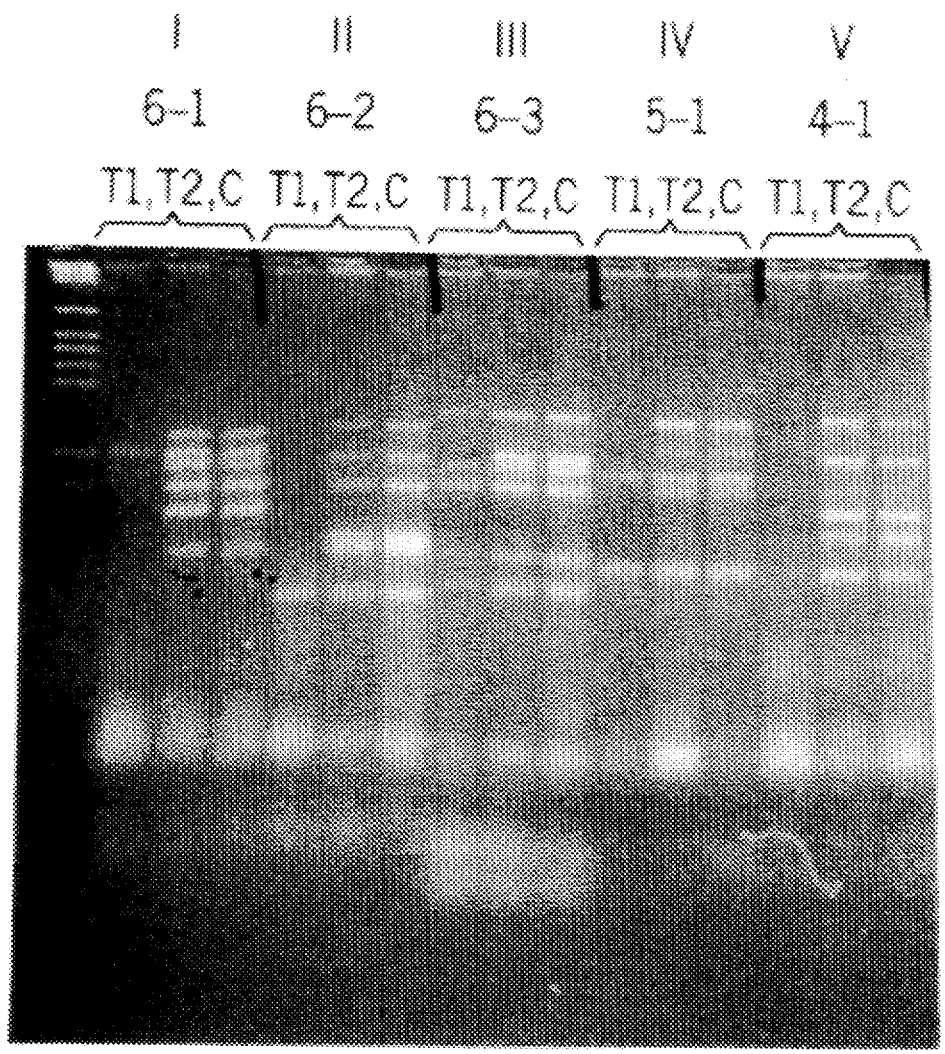
FIG. 5 is a photograph of working multiplexes I–V. In this gel, T-1 and T-2 refers to unborn "twins 1 and 2," respectively, and C refers to control male genomic DNA. DNA was extracted from amniocytes and screened by the presently claimed male infertility/Y-deletion detection system. Results: The twins are dizygotic. Twin 1 is missing all loci from interval 3 through interval 7 and Bkm. Twin 2 is a normal male with no deletions.

In FIG. 5, T-1 refers to the first twin, while T-2 refers to the second twin. C refers to control male genomic DNA. Analysis of the gel reveals the twins to be dizygotic. Comparison of the control lanes with the lanes for T-2 reveals Twin 2 to be a normal male with no deletions. In contrast, comparison of the control lanes with the T-1 lanes reveals that Twin 1 is missing all loci from interval 3 through interval 7, and BKM.

EXAMPLE 6

Multiplexes I–V Displaying a Deletion Event in Each Multiplex

Figure 6:
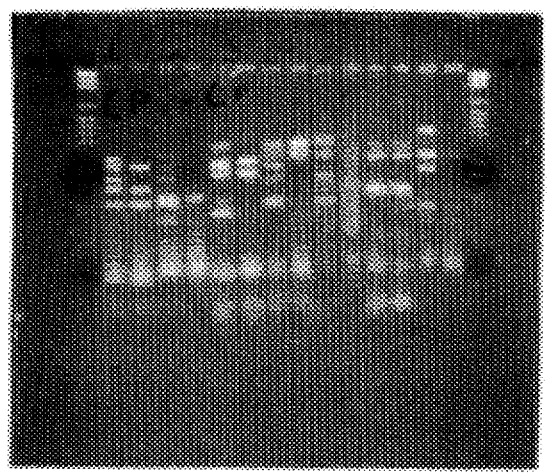
FIG. 6 is a photograph and example of working multiplexes. Samples are loaded from left to right as follows: Lane 1 Molecular Weight Control; Lane 2 Amplimer Ladder 1; Lane 3 Patient with deletions I; Lane 4 Amplimer Ladder 2; Lane 5 Patient with deletions II; Lane 6 Amplimer Ladder 3; Lane 7 Patient with deletions III; Lane 8 Amplimer Ladder 4; Lane 9 Patient with deletions IV; Lane 10 Amplimer Ladder 5; Lane 11 Patient with deletions V. The right-most lanes are an unrelated experiment.

In this example, amplimer ladders for each of the multiplexes I–V were developed in tandem with patients showing a deletion event in each of the multiplexes, respectively. The results are shown in FIG. 6. Going from left to right, the first lane is the molecular weight control, followed by paired lanes of amplimers of multiplexes I–V and patient DNA samples, respectively. The right-most pair of lanes is from an unrelated experiment.

EXAMPLE 7

Analysis of Normal Male DNA Using Multiplexes I, VI, X–XIII, XVII

Figure 7:
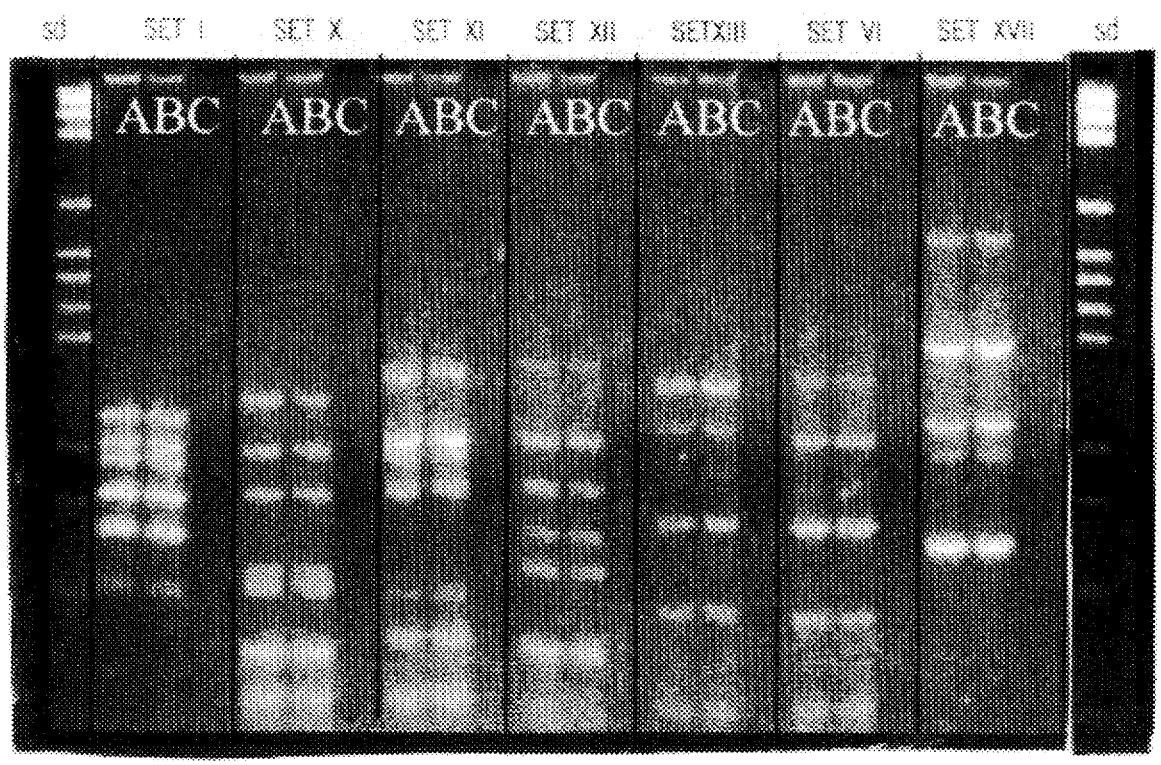
FIG. 7 is a photograph of working multiplexes I, VI, X–XIII, and XVII. For each multiplex, Lane A is amplified chromosomal DNA, Lane B is an amplimer ladder for the respective loci (positive control), and Lane C is a negative control. The lanes marked "sd" are molecular weight standards.

In this example, normal male chromosomal DNA was amplified using multiplexes I, VI, X–XIII, and XVII. The results are depicted in FIG. 7. Going from left to right, Lanes A, B, and C in each of the multiplexes are amplified chromosomal DNA, amplimer ladder DNA, and negative control, respectively. Molecular weight markers are contained in the lanes marked "sd." No deletion events are shown in the gel. This gel shows the clear resolution of loci accomplished by the disclosed multiplexes.

EXAMPLE 8

Repetitive Analysis Using Multiplex X

Figure 8:
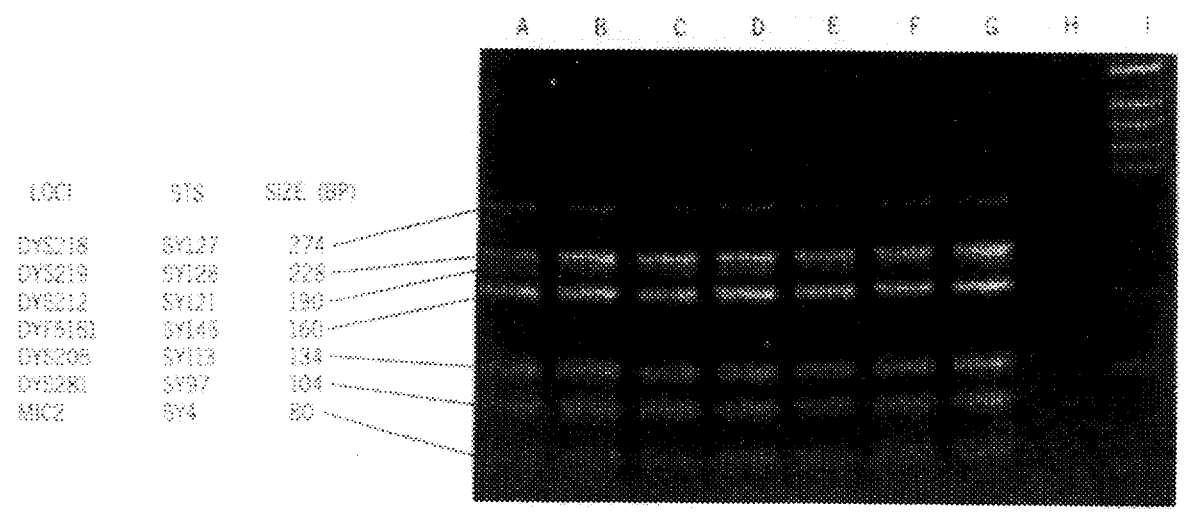
FIG. 8 is photograph of repetitive analyses using multiplex X. Lanes A–G contain DNA amplified with multiplex X. Lane H is a negative control containing no DNA. Lane I is a molecular weight standard. The seven loci amplified in Lanes A–G are, from top to bottom: DYS218, DYS219, DYS212, DYS51S1, DYS205, DYS281, and MIC2.
Figure 9:
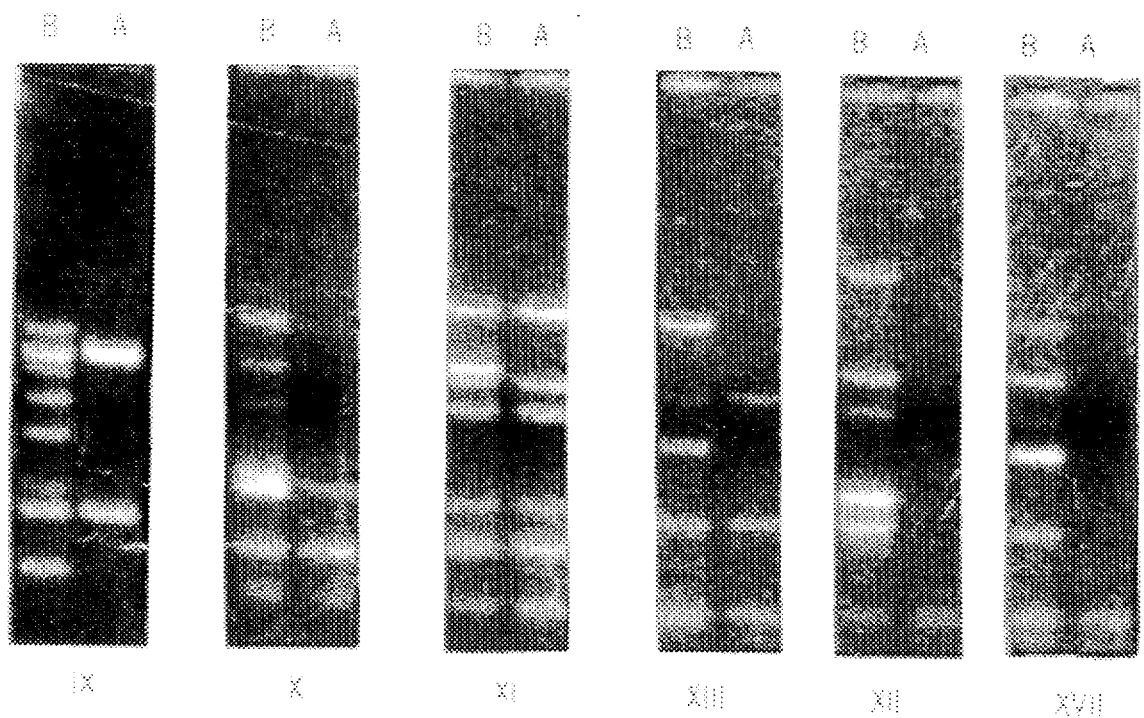
FIG. 9 is a photograph of an analysis of the twins described in FIG. 5, using multiplexes IX–XIII, and XVII. Here, "twins A and B," correspond to "twins 1 and 2," of FIG. 5, respectively. Twin A is shown to have a large number of deletion events as shown in the developed multiplex gels.

Here, duplicate runs using multiplex X were performed to illustrate the reproducibility of the multiplex. The results are shown in FIG. 8. Lanes A–G contain DNA amplified with multiplex X. Lane H contains a negative control. Lane I contains a molecular weight standard. FIG. 8 shows clean and reproducible separation of the loci contained within multiplex X.

EXAMPLE 9

Analysis of Prenatal Twins Utilizing Multiplexes IX–XIII and XVII

An analysis identical to that described in example 5 was performed utilizing multiplexes IX–XIII and XVII. Here, twins A and B correspond to twins 1 and 2 of example 5. Twin A shows numerous deletion events.

EXAMPLE 10

Schematic Representation of Y Deletion Events in Patient Population and in Twin A (Twin 1)

FIG. 3 depicts deletion breakpoints from a sample of patients screened. The Y chromosome regions and intervals are shown on the horizontal axis from left to right. Normal male and female and 8 patients are depicted from top to bottom on the vertical axis. Plus (+) signs show presence of the locus, minus (−) signs signify absence of the locus.

FIG. 10 shows an identical schematic for Twin A which displays numerous Y chromosome deletion events.

The present invention is not limited to the embodiments specifically enumerated above, but encompasses all such forms a variations thereof is are encompassed by the following claims.

BIBLIOGRAPHY

Ma, K., Sharkey, A., Kirsch, S., Vogt, P., Keil, R., Hargreave, T. B., McBeath, S., and Chandley, A. C. (1992) *Towards the molecular localisation of the AZF locus: mapping of microdeletions in azoospermic men within 14 subintervals of interval 6 of the human Y chromosome.* H. Mol. Gen. 1, 29–33.

Ma, K., Inglis, J. D., Sharkey, A., Bickmore, W. A., Hill, R. E., Prosser, E. J., Speed, R. M., Thomson, E. J., Jobling, M., Taylor, K., Wolfe, J., Cooke, H. J., Hargreave, T. B., and Chandley, A. C., (1993) *A Y Chromosome Gene Family with RNA-Binding Protein Homology: Candidates for the Azoospennia Factor AZF Controlling Human Spermatogenesis.* Cell 75, 1287–1295.

Agoulnik, A. I., Mitchell, M. J., Lerner, J. L., Woods, D. R., and Bishop, C. E. (1994) *A mouse Y chromosome gene encoded by a region essential for spermatogenesis and expression of male-specific minor histocompatibility antigens.* H. Mol. Gen. 3, 873–878.

Affara, N. A., Lau, Y. -F. C., Briggs, H., Davey, P., Jones, M. H., Khwaja, O., Mitchell, M., and Sargent, C. (1994) *Report of the First International Workshop on Y Chromosome Mapping 1994.* Cytogenet Cell Genet 67, 359–402.

Nagafuchi, S., Namiki, M., Nakahori, Y., Kondoh, N., Okuyama, A., and Nakagome, Y. (1993) *A Minute Deletion Of The Y Chromosome In Men With Azoospermia.* The J. of Urol. 150, 1155–1157.

Kobayashi, K., Mizuno, K., Hida, A., Komaki, R., Tomita, K., Matsishita, I., Namiki, M., Iwamoto, T., Tamura, S., Minowada, S., Nakahori, Y., and Nakagome, Y. (1994) *PCR analysis of the Y chromosome long arm in azoospermic patients: evidence for a second locus required for spermatogenesis.* H. Mol. Gen. 3, 1965–1967.

Henegariu, O., Hirschmann, P., Kilian, K., Kirsch, S., Lengauet, C., Maiwald, R., Mielke, K., and Vogt, P. (1994) *Rapid screening of the Y chromosome in idiopathic sterile men, diagnostic for deletions in AZF, a genetic Y factor expressed during spermatogenesis.* ANDROLOGIA 26, 97–106.

Chandley, A. C. and Cooke, H. J. (1994) *Human male fertility-Y-linked genes and spermatogenesis.* H. Mol. Gen. 3, 1449–1452.

---

What is claimed is:

1. A method for detecting deletions in a Y chromosome which are indicative of male infertility comprising:

(a) combining at least one plurality of distinct oligonucleotide primer pairs capable of priming at least one corresponding plurality of human X and Y chromosome loci selected from the group consisting of:

DYS209, DYF43S1, DYS210, DYS211, DYS33, DYS1, SMCX, DAZ(1);

DYS218, DYS219, DYS212, DYF53S1, DYS205, DYS281, MIC2;

DYS201, DYS241, DYS198, SRY, DYS197, DYS196, MIC2;

DYS240, DYS271, DYS221, KAL182, DAZ(2), MIC2;

DYS224, DYS226, DYS222, DYS227, MIC2;

DYF53S1, DYS229, DYZ1, DYS230, DAZ(3), DAZ(4), DAZ(5), MIC2;

SMCY, DYS217, DYS220, DYS223, DYS7, DYS237, DYS215, MIC2;

SMCY, DYS217, DYS220, DYS7, DYS237, DYS215, DAZ(6), MIC2;

DAZ(7), DAZ(8), DAZ(9), DAZ(10), DAZ(11), MIC2; and

YRRM1, SMCY, ZFY, BKM, SMCX;

with isolated genomic DNA of a test subject; then (b) amplifying the at least one plurality of distinct oligonucleotide primer pairs by at least one corresponding multiplex polymerase chain reaction to yield locus-specific amplified chromosomal DNA fragments; then (c) separating the amplified chromosomal DNA fragments; and then (d) comparing the amplified chromosomal DNA fragments to corresponding amplified chromosomal DNA fragments from normal male subjects, whereby deletions in the Y chromosome of the test subject are detected.

2. The method according to claim 1, wherein in step (a) the isolated genomic DNA of the test subject is combined with at least one plurality of distinct oligonucleotide primer pairs selected from the group consisting of:

SEQ. ID. NOS. 1-14, 95, and 96;

SEQ. ID. NOS. 15-26, 97, and 98;

SEQ. ID. NOS. 27-38, 97, and 98;

SEQ. ID. NOS. 39, 40, 43–48, 97–100;

SEQ. ID. NOS. 49–56, 97, and 98;

SEQ. ID. NOS. 59–62, 75, 76, 97, 98, and 115–122;

SEQ. ID. NOS. 71–74, 79–86, 97, 98, 101, and 102;

SEQ. ID. NOS. 71–74, 79, 80, 83–86, 97, 98, and 101–104;

SEQ. ID. NOS. 97, 98, and 105–114; and

SEQ. ID. NOS. 87–94, 13, and 14.

3. The method according to claim 2, wherein in step (a) the at least one plurality of distinct oligonucleotide primer pairs is combined with isolated genomic DNA of a human test subject.

4. The method according to claim 3, wherein in step (a) the at least one plurality of distinct oligonucleotide primer pairs is combined with isolated genomic DNA of a phenotypically male human test subject.

5. The method according to claim 3, wherein in step (a) the at least one plurality of distinct oligonucleotide primer pairs is combined with isolated genomic DNA of a human test subject of phenotypically ambiguous sexuality.

6. The method according to claim 3, wherein in step (a) the at least one plurality of distinct oligonucleotide primer pairs is combined with isolated genomic DNA of a phenotypically female human test subject.

7. The method according to claim 1, wherein in step (c), the amplified chromosomal DNA fragments are separated by gel electrophoresis.

8. The method according to claim 1, wherein in step (b) the at least one plurality of distinct oligonucleotide primer pairs amplified by at least one corresponding multiplex polymerase chain reaction are amplified by subjecting the at least one corresponding multiplex polymerase chain reaction to an initial denaturation at about 95° C. for about 2.5 minutes, and then cycling through 25 to 35 cycles of denaturation at about 95° C. for about 1 minute, annealing at about 61° C. for about 1 minute, and extension at about 72° C. for about 1 minute.

9. A method for detecting deletions in a Y chromosome which are indicative of male infertility comprising:

(a) combining ten pluralities of distinct oligonucleotide primer pairs capable of priming ten corresponding pluralities of human X and Y chromosome loci selected from the group consisting of:

DYS209, DYF43S1, DYS210, DYS211, DYS33, DYS1, SMCX, DAZ(1);

DYS218, DYS219, DYS212, DYF53S1, DYS205, DYS281, MIC2;

DYS201, DYS241, DYS198, SRY, DYS197, DYS196, MIC2;

DYS240, DYS271, DYS221, KAL182, DAZ(2), MIC2;

DYS224, DYS226, DYS222, DYS227, MIC2;

DYF53S1, DYS229, DYZ1, DYS230, DAZ(3), DAZ(4), DAZ(5), MIC2;

SMCY, DYS217, DYS220, DYS223, DYS7, DYS237, DYS215, MIC2;

SMCY, DYS217, DYS220, DYS7, DYS237, DYS215, DAZ(6), MIC2;

DAZ(7), DAZ(8), DAZ(9), DAZ(10), DAZ(11), MIC2; and

YRRM1, SMCY, ZFY, BKM, SMCX;

with isolated genomic DNA of a test subject, wherein each of the ten pluralities of distinct oligonucleotide primer pairs with its respective test subject genomic DNA are disposed within separate receptacles; then (b) amplifying the ten pluralities of distinct oligonucleotide primer pairs by ten corresponding multiplex polymerase chain reactions to yield locus-specific amplified chromosomal DNA fragments; then (c) separating the amplified chromosomal DNA fragments; and then (d) comparing the amplified chromosomal DNA fragments to corresponding amplified chromosomal DNA fragments from normal subjects, whereby deletions in the Y chromosome of the test subject are detected.

10. The method according to claim 9, wherein the isolated genomic DNA of the test subject is combined with the following ten pluralities of distinct oligonucleotide primer pairs:

SEQ. ID. NOS. 1–14, 95, and 96;

SEQ. ID. NOS. 15–26, 97, and 98;

SEQ. ID. NOS. 27–38, 97, and 98;

SEQ. ID. NOS. 39, 40, 43–48, 97–100;

SEQ. ID. NOS. 49–56, 97, and 98;

SEQ. ID. NOS. 59–62, 75, 76, 97, 98, and 115–122;

SEQ. ID. NOS. 71–74, 79–86, 97, 98, 101, and 102;

SEQ. ID. NOS. 71–74, 79, 80, 83–86, 97, 98, and 101–104;

SEQ. ID. NOS. 97, 98, and 105–114; and

SEQ. ID. NOS. 87–94, 13, and 14.

11. The method according to claim 10, wherein in step (a) the ten pluralities of distinct oligonucleotide primer pairs are combined with isolated genomic DNA of a human test subject.

12. The method according to claim 11, wherein in step (a) the ten pluralities of distinct oligonucleotide primer pairs are combined with isolated genomic DNA of a phenotypically male human test subject.

13. The method according to claim 11, wherein in step (a) the ten pluralities of distinct oligonucleotide primer pairs are combined with isolated genomic DNA of a human test subject of phenotypically ambiguous sexuality.

14. The method according to claim 11, wherein in step (a) the ten pluralities of distinct oligonucleotide primer pairs are combined with isolated genomic DNA of a human male test subject with infertility due to azoospermia or oligospermia.

15. The method according to claim 11, wherein in step (a) the ten pluralities of distinct oligonucleotide primer pairs are combined with isolated genomic DNA of a phenotypically female human test subject.

16. The method according to claim 9, wherein in step (c), the amplified chromosomal DNA fragments are separated by gel electrophoresis.

17. The method according to claim 10, wherein in step (b) the ten pluralities of distinct primer pairs within the ten corresponding multiplex polymerase chain reactions are amplified by subjecting the ten corresponding multiplex polymerase chain reactions to an initial denaturation at about 95° C. for about 2.5 minutes, and then cycling through 25 to 35 cycles of denaturation at about 95° C. for about 1 minute, annealing at about 61° C. for about 1 minute, and extension at about 72° C. for about 1 minute.

18. A kit for detecting deletion mutations on a Y chromosome which are indicative of male infertility comprising:

at least one first receptacle containing at least one corresponding plurality of locus-specific oligonucleotide primer pairs, said at least one corresponding plurality of oligonucleotide primer pairs capable of specifically priming at least one corresponding plurality of human X and Y chromosome loci selected from the group consisting of:

DYS209, DYF43S1, DYS210, DYS211, DYS33, DYS1, SMCX, DAZ(1);

DYS218, DYS219, DYS212, DYF53S1, DYS205, DYS281, MIC2;

DYS201, DYS241, DYS198, SRY, DYS197, DYS196, MIC2;

DYS240, DYS271, DYS221, KAL182, DAZ(2), MIC2;

DYS224, DYS226, DYS222, DYS227, MIC2;

DYF53S1, DYS229, DYZ1, DYS230, DAZ(3), DAZ(4), DAZ(5), MIC2;

SMCY, DYS217, DYS220, DYS223, DYS7, DYS237, DYS215, MIC2;

SMCY, DYS217, DYS220, DYS7, DYS237, DYS215, DAZ(6), MIC2;

DAZ(7), DAZ(8), DAZ(9), DAZ(10), DAZ(11), MIC2; and

YRRM1, SMCY, ZFY, BKM, SMCX;

at least one second receptacle containing at least one control DNA amplimer ladder corresponding to said at least one plurality of human X and Y chromosome loci; and instructions for use.

19. The kit according to claim 18, wherein said at least one corresponding plurality of oligonucleotide primer pairs is selected from the group consisting of:

SEQ. ID. NOS. 1–14, 95, and 96;
SEQ. ID. NOS. 15–26, 97, and 98;
SEQ. ID. NOS. 27–38, 97, and 98;
SEQ. ID. NOS. 39, 40, 43–48, 97–100;
SEQ. ID. NOS. 49–56, 97, and 98;
SEQ. ID. NOS. 59–62, 75, 76, 97, 98, and 115–122;
SEQ. ID. NOS. 71–74, 79–86, 97, 98, 101, and 102;
SEQ. ID. NOS. 71–74, 79, 80, 83–86, 97, 98, and 101–104;
SEQ. ID. NOS. 97, 98, and 105–114; and
SEQ. ID. NOS. 87–94, 13, and 14.

20. The kit according to claim 18, further comprising a supply of nanopure water, a supply of PCR-suitable buffer, a supply of PCR-suitable magnesium, and a supply of PCR-suitable dNTP's.

21. The kit according to claim 19, further comprising at least one third receptacle, wherein said supplies of nanopure water, PCR-suitable buffer, PCR-suitable magnesium, and PCR-suitable dNTP's are combined together at PCR-suitable concentrations and disposed therein.

22. The kit according to claim 18, wherein said at least one corresponding plurality of oligonucleotide primer pairs and said at least one control DNA amplimer ladder are contained respectively in said at least one first receptacle and said at least one second receptacle, in combination with PCR-suitable concentrations of nanopure water, PCR-suitable buffer, PCR-suitable magnesium, and PCR-suitable dNTP's.

23. The kit according to claim 18, further comprising a plurality of pre-sterilized microfuge receptacles.

24. The kit according to claim 18, further comprising a supply of Taq DNA polymerase.

25. The kit according to claim 18, further comprising a supply of sterile mineral oil.

26. The kit according to claim 18, further comprising a supply of molecular weight DNA control markers.

27. The kit according to claim 18, further comprising a supply of gel electrophoresis loading dye.

28. The kit according to claim 18, further comprising a supply of normal human female DNA, and a supply of normal human male DNA.

29. The kit according to claim 18, further comprising:

ten first receptacles containing ten corresponding pluralities of oligonucleotide primer pairs capable of priming ten pluralities of human Y chromosome loci and non-Y linked control loci as follows:

DYS209, DYF43S1, DYS210, DYS211, DYS33, DYS1, SMCX, DAZ(1);

DYS218, DYS219, DYS212, DYF53S1, DYS205, DYS281, MIC2;

DYS201, DYS241, DYS198, SRY, DYS197, DYS196, MIC2;

DYS240, DYS271, DYS221, KAL182, DAZ(2), MIC2;

DYS224, DYS226, DYS222, DYS227, MIC2;

DYF53S1, DYS229, DYZ1, DYS230, DAZ(3), DAZ(4), DAZ(5), MIC2;

SMCY, DYS217, DYS220, DYS223, DYS7, DYS237, DYS215, MIC2;

SMCY, DYS217, DYS220, DYS7, DYS237, DYS215, DAZ(6), MIC2;

DAZ(7), DAZ(8), DAZ(9), DAZ(10), DAZ(11), MIC2; and

YRRM1, SMCY, ZFY, BKM, SMCX;

ten second receptacles containing ten control DNA amplimer ladders corresponding to said ten pluralities of human Y chromosome loci and non-Y linked control loci.

30. The kit according to claim 28, wherein said ten corresponding pluralities of oligonucleotide primer pairs are:

SEQ. ID. NOS. 1–14, 95, and 96;
SEQ. ID. NOS. 15–26, 97, and 98;
SEQ. ID. NOS. 27–38, 97, and 98;
SEQ. ID. NOS. 39, 40, 43–48, 97–100;
SEQ. ID. NOS. 49–56, 97, and 98;
SEQ. ID. NOS. 59–62, 75, 76, 97, 98, and 115–122;
SEQ. ID. NOS. 71–74, 79–86, 97, 98, 101, and 102;
SEQ. ID. NOS. 71–74, 79, 80, 83–86, 97, 98, and 101–104;
SEQ. ID. NOS. 97, 98, and 105–114; and
SEQ. ID. NOS. 87–94, 13, and 14.

31. The kit according to claim 28, further comprising a supply of nanopure water, a supply of PCR-suitable buffer, a supply of PCR--suitable magnesium, and a supply of PCR-suitable dNTP'S.

32. The kit according to claim 30, further comprising at least one third receptacle, wherein said supplies of nanopure water, PCR-suitable buffer, PCR-suitable magnesium, and PCR-suitable dNTP's are combined together at PCR-suitable concentrations and disposed therein.

33. The kit according to claim 28, wherein said ten corresponding pluralities of oligonucleotide primer pairs and said ten control DNA amplimer ladders are contained respectively in said ten first receptacles and said ten second receptacles, in combination with PCR-suitable concentrations of nanopure water, PCR-suitable buffer, PCR-suitable magnesium, and PCR-suitable dNTP's.

34. The kit according to claim 28, further comprising a plurality of pre-sterilized microfuge receptacles.

35. The kit according to claim 28, further comprising a supply of Taq DNA polymerase.

36. The kit according to claim 28, further comprising a supply of sterile mineral oil.

37. The kit according to claim 28, further comprising a supply of molecular weight DNA control markers.

38. The kit according to claim 28, further comprising a supply of gel electrophoresis loading dye.

39. The kit according to claim 28, further comprising a supply of normal human female DNA, and a supply of normal human male DNA.

40. A system for assessing the integrity of specific regions on the human Y chromosome, which regions are associated with human male infertility, comprising:

at least one first receptacle containing at least one corresponding plurality of oligonucleotide primer pairs, said at least one corresponding plurality of oligonucleotide primer pairs capable of priming at least one corresponding plurality of human X and Y chromosome loci selected from the group consisting of:

DYS209, DYF43S1, DYS210, DYS211, DYS33, DYS1, SMCX, DAZ(1);

DYS218, DYS219, DYS212, DYF53S1, DYS205, DYS281, MIC2;

DYS201, DYS241, DYS198, SRY, DYS197, DYS196, MIC2;

DYS240, DYS271, DYS221, KAL182, DAZ(2), MIC2;

DYS224, DYS226, DYS222, DYS227, MIC2;

DYF53S1, DYS229, DYZ1, DYS230, DAZ(3), DAZ(4), DAZ(5), MIC2;

SMCY, DYS217, DYS220, DYS223, DYS7, DYS237, DYS215, MIC2;

SMCY, DYS217, DYS220, DYS7, DYS237, DYS215, DAZ(6), MIC2;

DAZ(7), DAZ(8), DAZ(9), DAZ(10), DAZ(11), MIC2; and

YRRM1, SMCY, ZFY, BKM, SMCX;

at least one second receptacle containing at least one control DNA amplimer ladder corresponding to said at least one plurality of human X and Y chromosome loci;

a third receptacle containing normal human female DNA;

a fourth receptacle containing normal human female DNA; and instructions for use.

* * * * *

SEQUENCE LISTING ( 1 ) GENERAL INFORMATION:

( i i i ) NUMBER OF SEQUENCES: 124

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GTTGGTTCCA TGCTCCATAC         20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GTTGGTTCCA TGCTCCATAC         20

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AGGAGATGTC AGGACTATCA GC         22

( 2 ) INFORMATION FOR SEQ ID NO:4:

( i ) SEQUENCE CHARACTERISTICS:

(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

TCCATCCAGC TGGTCATATT                           20

(2) INFORMATION FOR SEQ ID NO:5:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

GTACCTCTGC AGGCACTGAT                           20

(2) INFORMATION FOR SEQ ID NO:6:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

ACACAATCCA ACCTGGCTAA                           20

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

AGGCTCCATC TGTAGCACAC                           20

(2) INFORMATION FOR SEQ ID NO:8:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

TAACCTTATA GACCAACCCC G                         21

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:9:

TCCATCTGTT GCTCCCCTAC                                                        20

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:10:

ACTATCAAAC AGCCAGCCAA G                                                      21

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:11:

TGTCACACTG CCCTAATCCT                                                        20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:12:

TGGTCATGAC AAAAGACGAA                                                        20

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:13:

TGTGATGGCT GTGATGACAA C                                                      21

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:14:

ACACACTTTG GGCACCTCCA                                                        20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GGCTCACAAA CGAAAAGAAA     20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CTGCAGGCAG TAATAAGGGA     20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CTGCAGGCAG TAATAAGGGA     20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

AGCCCAATGT AAACTGGACA     20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

AGTTCACAGA ATGGAGCCTG     20

( 2 ) INFORMATION FOR SEQ ID NO:20:

( i ) SEQUENCE CHARACTERISTICS:

( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

CCTGTGACTC CAGTTTGGTC 20

( 2 ) INFORMATION FOR SEQ ID NO:21:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CAACACAAAA ACACTCATAT ACTCG 25

( 2 ) INFORMATION FOR SEQ ID NO:22:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

TTGAGAATAA TTGTATGTTA CGGG 24

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

GGCTAGGTGC CAGCAAGTAG ATCA 24

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

GTTCTCTTCC CCTGCATCAA G 21

( 2 ) INFORMATION FOR SEQ ID NO:25:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (  i  i  )  MOLECULE TYPE: DNA (genomic)

(  x  i  )  SEQUENCE DESCRIPTION: SEQ ID NO:25:

AACTTCATCA GTGTTACATC AAGG 24

( 2 ) INFORMATION FOR SEQ ID NO:26:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:26:

TGTGGCATTT TGTTATGTGG 20

( 2 ) INFORMATION FOR SEQ ID NO:27:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:27:

AAGGGCTTCT TCTCTTGCTT 20

( 2 ) INFORMATION FOR SEQ ID NO:28:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:28:

AGGGAGCTTA AACTCACCGT 20

( 2 ) INFORMATION FOR SEQ ID NO:29:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:29:

CTCAGAAGTC CTCCTAATAG TTCC 24

( 2 ) INFORMATION FOR SEQ ID NO:30:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:30:

ACAGTGGTTT GTAGCGGGTA 20

( 2 ) INFORMATION FOR SEQ ID NO:31:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

CACTACCACA TTTCTGGTTG G          21

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

CGCTGAGTCC ATTCTTTGAG          20

( 2 ) INFORMATION FOR SEQ ID NO:33:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

GAATATTCCC GCTCTCCGGA          20

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

GCTGGTGCTC CATTCTTGAG          20

( 2 ) INFORMATION FOR SEQ ID NO:35:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

TTTTGCACCT TCACAGATGA          20

( 2 ) INFORMATION FOR SEQ ID NO:36:

( i ) SEQUENCE CHARACTERISTICS:

```
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:36:

TTCATTGAAA GCTGACACGA                                                         20

( 2 ) INFORMATION FOR SEQ ID NO:37:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:37:

TAAAGGAACT TCTGTGTGTA AACA                                                    24

( 2 ) INFORMATION FOR SEQ ID NO:38:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:38:

TAAGCCAGAT AGGGGCTTCT                                                         20

( 2 ) INFORMATION FOR SEQ ID NO:39:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:39:

CTTAGGAAAA AGTGAAGCCG                                                         20

( 2 ) INFORMATION FOR SEQ ID NO:40:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:40:

CCTGCTGTCA GCAAGATACA                                                         20

( 2 ) INFORMATION FOR SEQ ID NO:41:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear
```

( i i ) MOLECULE TYPE: DNA (genomic)

( x i ) SEQUENCE DESCRIPTION: SEQ ID NO:41:

TTTGCACCAG GATTAAGTGA                                               20

( 2 ) INFORMATION FOR SEQ ID NO:42:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:42:

TTTTTTCAGA TAAACTTTCA GTGG                                          24

( 2 ) INFORMATION FOR SEQ ID NO:43:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:43:

AGGCACTGGT CAGAATGAAG                                               20

( 2 ) INFORMATION FOR SEQ ID NO:44:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:44:

AATGGAAAAT ACAGCTCCCC                                               20

( 2 ) INFORMATION FOR SEQ ID NO:45:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:45:

AGAGAGTTTT CTAACAGGGC G                                             21

( 2 ) INFORMATION FOR SEQ ID NO:46:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:46:

TGGGAATCAC TTTTGCAACT                                               20

( 2 ) INFORMATION FOR SEQ ID NO:47:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

TCAGAAGTGA AACCCTGTAT G                                                  21

( 2 ) INFORMATION FOR SEQ ID NO:48:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

GCATGTGACT CAAAGTATAA GC                                           22

( 2 ) INFORMATION FOR SEQ ID NO:49:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

GTCTGCCTCA CCATAAAACG                                              20

( 2 ) INFORMATION FOR SEQ ID NO:50:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

ACCACTGCCA AAACTTTCAA                                              20

( 2 ) INFORMATION FOR SEQ ID NO:51:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

CACATGAAGC ACTGGAACTG                                              20

( 2 ) INFORMATION FOR SEQ ID NO:52:

( i ) SEQUENCE CHARACTERISTICS:

( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:52:

GTTGTCTGGA AATCCCTGTG                                                                  20

( 2 ) INFORMATION FOR SEQ ID NO:53:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:53:

ACATATCCCT TGCCACTTCA                                                                  20

( 2 ) INFORMATION FOR SEQ ID NO:54:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:54:

TCAGGTACCT TCTGCCTGAG                                                                  20

( 2 ) INFORMATION FOR SEQ ID NO:55:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:55:

TTCAGAGGAA TCATGTGGGT                                                                  20

( 2 ) INFORMATION FOR SEQ ID NO:56:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:56:

AATGTTTCAT CACCATTATC CC                                                               22

( 2 ) INFORMATION FOR SEQ ID NO:57:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:57:

AGGGTAAAAT GCATAAGCCC 20

( 2 ) INFORMATION FOR SEQ ID NO:58:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

TTATCCTGCT GCTGGGTAAG 20

( 2 ) INFORMATION FOR SEQ ID NO:59:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

TACGGGTCTC GAATGGAATA 20

( 2 ) INFORMATION FOR SEQ ID NO:60:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:60:

TCATTGCATT CCTTTCCATT 20

( 2 ) INFORMATION FOR SEQ ID NO:61:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

AGCTTCTATT CGAGGGCTTC 20

( 2 ) INFORMATION FOR SEQ ID NO:62:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:62:

CTCTCTGCAA TCCCTGACAT 20

( 2 ) INFORMATION FOR SEQ ID NO:63:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

CACATGAAGC ACTGGAACTG     20

( 2 ) INFORMATION FOR SEQ ID NO:64:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

AGGGCCTGAG TCTCCAGG     18

( 2 ) INFORMATION FOR SEQ ID NO:65:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:65:

TCATCTGCCA CCATCAACAT     20

( 2 ) INFORMATION FOR SEQ ID NO:66:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:66:

ACGTGTTTCT ACACCTGCCC     20

( 2 ) INFORMATION FOR SEQ ID NO:67:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:67:

ACAAGTCCTC AAACACACTG G     21

( 2 ) INFORMATION FOR SEQ ID NO:68:

( i ) SEQUENCE CHARACTERISTICS:

( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:68:

CTCCATGCTT GCTTTTCTC                               20

( 2 ) INFORMATION FOR SEQ ID NO:69:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:69:

AATGTGCCCA CACAGAGTTC                              20

( 2 ) INFORMATION FOR SEQ ID NO:70:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:70:

TGGAAGACCA GGATTTCATG                              20

( 2 ) INFORMATION FOR SEQ ID NO:71:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:71:

GTGGTCTGTG GAAGGTGTCA                              20

( 2 ) INFORMATION FOR SEQ ID NO:72:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:72:

CCTCCAGACC TGGACAGAAT T                            21

( 2 ) INFORMATION FOR SEQ ID NO:73:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:73:

AAAAATGAGT GGCACTATGT ACA 23

( 2 ) INFORMATION FOR SEQ ID NO:74:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:74:

CTGCAGGCAG TAATAAGGGA 20

( 2 ) INFORMATION FOR SEQ ID NO:75:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:75:

GCAGTTCCAT TGTTTGCTTC 20

( 2 ) INFORMATION FOR SEQ ID NO:76:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:76:

GCAGCATAAT AGCTATACAG TATGG 25

( 2 ) INFORMATION FOR SEQ ID NO:77:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:77:

TAATCAGTCT CCTCCCAGCA 20

( 2 ) INFORMATION FOR SEQ ID NO:78:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:78:

AAAATTGTGA ATCTGAAATT TAAGG 25

( 2 ) INFORMATION FOR SEQ ID NO:79:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:79:

AGCTTCAGGA GGTTCAAAAC                                      20

( 2 ) INFORMATION FOR SEQ ID NO:80:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:80:

AAGTGGGACC TAAGCTACGA                                      20

( 2 ) INFORMATION FOR SEQ ID NO:81:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:81:

GGGAGAGTCA CATCACTTGG                                      20

( 2 ) INFORMATION FOR SEQ ID NO:82:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:82:

TTGAATTATC TGCCTGAGTG C                                     21

( 2 ) INFORMATION FOR SEQ ID NO:83:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:83:

GCATCCTCAT TTTATGTCCA                                      20

( 2 ) INFORMATION FOR SEQ ID NO:84:

( i ) SEQUENCE CHARACTERISTICS:

(A) LENGTH: 20 base pairs
          (B) TYPE: nucleic acid
          (C) STRANDEDNESS: single
          (D) TOPOLOGY: linear (i i) MOLECULE TYPE: DNA (genomic)

(x i) SEQUENCE DESCRIPTION: SEQ ID NO:84:

CAACCCAAAA GCACTGAGTA                    20

(2) INFORMATION FOR SEQ ID NO:85:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (i i) MOLECULE TYPE: DNA (genomic)

(x i) SEQUENCE DESCRIPTION: SEQ ID NO:85:

CAGGCAGGAC AGCTTAAAAG                    20

(2) INFORMATION FOR SEQ ID NO:86:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (i i) MOLECULE TYPE: DNA (genomic)

(x i) SEQUENCE DESCRIPTION: SEQ ID NO:86:

ACTGTGGCAA AGTTGCTTTC                    20

(2) INFORMATION FOR SEQ ID NO:87:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (i i) MOLECULE TYPE: DNA (genomic)

(x i) SEQUENCE DESCRIPTION: SEQ ID NO:87:

AGAGGCACTT CAGAGATACG G                  21

(2) INFORMATION FOR SEQ ID NO:88:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (i i) MOLECULE TYPE: DNA (genomic)

(x i) SEQUENCE DESCRIPTION: SEQ ID NO:88:

CTTTGAAAAC AATTCCTTTT CC                 22

(2) INFORMATION FOR SEQ ID NO:89:

(i) SEQUENCE CHARACTERISTICS:
          (A) LENGTH: 22 base pairs
          (B) TYPE: nucleic acid
          (C) STRANDEDNESS: single
          (D) TOPOLOGY: linear ( i i ) MOLECULE TYPE: DNA (genomic)

( x i ) SEQUENCE DESCRIPTION: SEQ ID NO:89:

AACTGTACTC CTGGGTAGCC TG 22

( 2 ) INFORMATION FOR SEQ ID NO:90:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:90:

CTCCCGTGGG GATGAAGATA ATA 23

( 2 ) INFORMATION FOR SEQ ID NO:91:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:91:

GGGAAGCTTG ACTGTCTATC CTTGCA 26

( 2 ) INFORMATION FOR SEQ ID NO:92:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:92:

GGGGAATTCT CGCCGGTATG GATTCGC 27

( 2 ) INFORMATION FOR SEQ ID NO:93:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:93:

ACCATTGCTC TCTGTATTCC 20

( 2 ) INFORMATION FOR SEQ ID NO:94:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:94:

CAATCGAAAC GAAAGGCA 18

( 2 ) INFORMATION FOR SEQ ID NO:95:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:95:

CTCTGGGACA AGTGTTCCTT G    21

( 2 ) INFORMATION FOR SEQ ID NO:96:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:96:

CATTGGCATG AATGTGTATT CA    22

( 2 ) INFORMATION FOR SEQ ID NO:97:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:97:

CGGGGAGGAG ACAGAGGGGG TAGG    24

( 2 ) INFORMATION FOR SEQ ID NO:98:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:98:

CTGAGAAGGG GCGGGGCGTG TA    22

( 2 ) INFORMATION FOR SEQ ID NO:99:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:99:

TGTTGTACGT AGAAAAAGGA TATTTACC    29

( 2 ) INFORMATION FOR SEQ ID NO:100:

( i ) SEQUENCE CHARACTERISTICS:

(A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:100:

ATATGGTAAA CCACTTTTTA AAATTGCCA 29

(2) INFORMATION FOR SEQ ID NO:101:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:101:

GAGAGTCATA ATGCCGACGT 20

(2) INFORMATION FOR SEQ ID NO:102:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:102:

TGGTCTCAGG AAGTTTTTGC 20

(2) INFORMATION FOR SEQ ID NO:103:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:103:

CATTGGCATG AATGTGTATT C 21

(2) INFORMATION FOR SEQ ID NO:104:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:104:

CTCTGGGACA AGTGTTCCTT 20

(2) INFORMATION FOR SEQ ID NO:105:

(i) SEQUENCE CHARACTERISTICS:
        (A) LENGTH: 20 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:105:

GGGTGTTACC AGAAGGCAAA                    20

( 2 ) INFORMATION FOR SEQ ID NO:106:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:106:

GAACCGTATC TACCAAAGCA GC                    22

( 2 ) INFORMATION FOR SEQ ID NO:107:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:107:

ACACAGTAGC AGCGGGAGTT                    20

( 2 ) INFORMATION FOR SEQ ID NO:108:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:108:

TCTGCCACTA AACTGTAAGC TCC                    23

( 2 ) INFORMATION FOR SEQ ID NO:109:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:109:

CATTCATCTT CCCTTTTGAA GG                    22

( 2 ) INFORMATION FOR SEQ ID NO:110:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:110:

ATGCAAGTCG CAGGAAATCT                    20

( 2 ) INFORMATION FOR SEQ ID NO:111:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:111:

GGACATAGTC CTGCTTAAGA AAAAGTGG                                            28

( 2 ) INFORMATION FOR SEQ ID NO:112:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:112:

ACGTGGTTCA GGAGGTCTAC TATTCTA                                             27

( 2 ) INFORMATION FOR SEQ ID NO:113:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:113:

GTTACAGGAT TCGGCGTGAT                                                          20

( 2 ) INFORMATION FOR SEQ ID NO:114:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:114:

CTCGTCATGT GCAGCCAC                                                            18

( 2 ) INFORMATION FOR SEQ ID NO:115:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:115:

ATTTTGCCTT GCATTGCTAG                                                        20

( 2 ) INFORMATION FOR SEQ ID NO:116:

( i ) SEQUENCE CHARACTERISTICS:

( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:116:

TTTTTAAGCC TGTGACCTGG 20

( 2 ) INFORMATION FOR SEQ ID NO:117:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:117:

ATTGATGTGT TGCCCCAAAT 20

( 2 ) INFORMATION FOR SEQ ID NO:118:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:118:

AGAGTGAACT TTAAATCCCA GCC 23

( 2 ) INFORMATION FOR SEQ ID NO:119:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:119:

ACAGTTTGAA ATGAAATTTT AAATGTGTT 29

( 2 ) INFORMATION FOR SEQ ID NO:120:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:120:

TGACAAAGTG AGACCCTACT ACTA 24

( 2 ) INFORMATION FOR SEQ ID NO:121:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear -continued ( i i ) MOLECULE TYPE: DNA (genomic)

( x i ) SEQUENCE DESCRIPTION: SEQ ID NO:121:

AGCTCACTGC AAGCAACAGA                                                                          20

( 2 ) INFORMATION FOR SEQ ID NO:122:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:122:

CCACCATCCC CCTTCTTC                                                                            18

( 2 ) INFORMATION FOR SEQ ID NO:123:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:123:

ATTTCTCTGC CCTTCACCAG                                                                          20

( 2 ) INFORMATION FOR SEQ ID NO:124:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:124:

TGATGATTGC CTAAAGGGAA                                                                          20